US006290728B1

(12) United States Patent
Phelps et al.

(10) Patent No.: US 6,290,728 B1
(45) Date of Patent: Sep. 18, 2001

(54) DESIGNS FOR LEFT VENTRICULAR CONDUIT

(75) Inventors: David Y. Phelps; Greg R. Furnish, both of Louisville; Todd A. Hall, Goshen; Mark Griffin, Louisville, all of KY (US); Scott J. Wolf, Minneapolis, MN (US); Peter J. Wilk, New York, NY (US); Jay Schmelter, Plymouth, MN (US); Simon Furnish, Louisville, KY (US)

(73) Assignee: Percardia, Inc., Nashua, NH (US)

( * ) Notice: Subject to any disclaimer, the term of this patent is extended or adjusted under 35 U.S.C. 154(b) by 0 days.

(21) Appl. No.: 09/369,048

(22) Filed: Aug. 4, 1999

Related U.S. Application Data
(60) Provisional application No. 60/099,767, filed on Sep. 10, 1998, and provisional application No. 60/104,397, filed on Oct. 15, 1998.

(51) Int. Cl.⁷ .................................................. A61F 2/06
(52) U.S. Cl. ........................... 623/23.7; 623/1.15; 604/8
(58) Field of Search .............................. 623/1.14, 1.16, 623/1.15, 23.7, 23.64, 194; 606/194, 108; 604/8

(56) References Cited

U.S. PATENT DOCUMENTS

| 4,503,568 | 3/1985 | Madras . |
| 4,733,665 | 3/1988 | Palmaz . |

(List continued on next page.)

FOREIGN PATENT DOCUMENTS

| 0 732 088 | 9/1996 | (EP) . |
| 0 824 903 | 2/1998 | (EP) . |
| 0 876 803 | 11/1998 | (EP) . |
| 0 903 123 | 3/1999 | (EP) . |
| 0 904 745 | 3/1999 | (EP) . |
| 0 955 017 | 11/1999 | (EP) . |
| 0 955 019 | 11/1999 | (EP) . |
| 0 962 194 | 12/1999 | (EP) . |

(List continued on next page.)

OTHER PUBLICATIONS

Gardner, M.D. et al., "An Experimental Anatomic Study of Indirect Myocardial Revascularization", *Journal of Surgical Research*, May 1971, vol. 11, No. 5, pp. 243–247.

Palmaz et al., "Expandable Intrahepatic Portacaval Shunt Stents: Early Experience in the Dog", *AJR*, vol. 145, pp. 821–825.

Palmaz et al., "Expandable Intrahepatic Portacaval Shunt Stents in Dogs with Chronic Portal Hypertension, " *AJR*, vol. 147, pp. 1251–1254.

Richter, M.D. et al., "Transjugular Intrahepatic Portacaval Stent Shunt: Preliminary Clinical Results," *Radiology*, 1990, vol. 174, No. 3, pp. 1027–1030.

(List continued on next page.)

*Primary Examiner*—David H. Willse
*Assistant Examiner*—Suzette J. Jackson
(74) *Attorney, Agent, or Firm*—Finnegan, Henderson, Farabow, Garrett & Dunner, L.L.P.

(57) ABSTRACT

A conduit is provided to provide a bypass around a blockage in the coronary artery. The conduit is adapted to be positioned in the myocardium or heart wall to provide a passage for blood to flow between a chamber of the heart such as the left ventricle and the coronary artery, distal to the blockage. The stent is self-expanding or uses a balloon to expand the stent in the heart wall. Various attachment means are provided to anchor the stent and prevent its migration.

12 Claims, 27 Drawing Sheets

U.S. PATENT DOCUMENTS

| | | |
|---|---|---|
| 4,769,029 | 9/1988 | Patel . |
| 4,995,857 | 2/1991 | Arnold . |
| 5,035,702 | 7/1991 | Taheri . |
| 5,135,467 | 8/1992 | Citron . |
| 5,258,008 | 11/1993 | Wilk . |
| 5,287,861 | 2/1994 | Wilk . |
| 5,330,486 | 7/1994 | Wilk . |
| 5,344,426 | 9/1994 | Lau et al. . |
| 5,384,541 | 1/1995 | Kirsch et al. . |
| 5,409,019 | 4/1995 | Wilk . |
| 5,423,744 | 6/1995 | Samuels . |
| 5,429,144 | 7/1995 | Wilk . |
| 5,443,497 | 8/1995 | Venbrux . |
| 5,456,712 | 10/1995 | Maginot . |
| 5,456,714 | 10/1995 | Owen . |
| 5,470,320 | 11/1995 | Tifenbrun et al. . |
| 5,527,337 | 6/1996 | Stack et al. . |
| 5,554,119 | 9/1996 | Harrison et al. . |
| 5,578,075 | 11/1996 | Dayton . |
| 5,593,434 | 1/1997 | Williams . |
| 5,609,626 | 3/1997 | Quijano et al. . |
| 5,618,299 | 4/1997 | Khorsavi et al. . |
| 5,655,548 | 8/1997 | Nelson et al. . |
| 5,662,124 | 9/1997 | Wilk . |
| 5,755,682 | 5/1998 | Knudson . |
| 5,758,663 | 6/1998 | Wilk et al. . |
| 5,797,933 | 8/1998 | Snow et al. . |
| 5,810,836 | 9/1998 | Hussein et al. . |
| 5,824,038 | 10/1998 | Wall . |
| 5,824,071 | 10/1998 | Nelson et al. . |
| 5,830,222 | 11/1998 | Makower . |
| 5,843,163 | 12/1998 | Wall . |
| 5,851,232 | 12/1998 | Lois . |
| 5,855,597 | 1/1999 | Javaraman . |
| 5,865,723 | 2/1999 | Love . |
| 5,876,419 | 3/1999 | Carpenter et al. . |
| 5,878,751 | 3/1999 | Hussein et al. . |
| 5,908,028 | 6/1999 | Wilk . |
| 5,908,029 | 6/1999 | Knudson et al. . |
| 5,935,119 | 8/1999 | Guy et al. . |
| 5,935,161 | 8/1999 | Robinson et al. . |
| 5,935,162 | 8/1999 | Dang . |
| 5,944,019 | 8/1999 | Knudson et al. . |
| 5,961,548 | 10/1999 | Shmulewitz . |
| 5,968,093 | 10/1999 | Kranz . |
| 5,971,993 * | 10/1999 | Hussein et al. ................. 606/108 |
| 5,976,159 | 11/1999 | Bolduc et al. . |
| 5,976,169 | 11/1999 | Imran . |
| 5,976,181 | 11/1999 | Whelan et al. . |
| 5,976,182 | 11/1999 | Cox . |
| 5,976,192 | 11/1999 | McIntyre et al. . |
| 5,976,650 | 11/1999 | Campbell et al. . |
| 5,979,455 | 11/1999 | Maginot . |
| 5,980,548 | 11/1999 | Evans et al. . |
| 5,980,551 * | 11/1999 | Summers et al. ................. 606/194 |
| 5,980,552 | 11/1999 | Pinchasik et al. . |
| 5,980,553 | 11/1999 | Gray et al. . |
| 5,980,566 | 11/1999 | Alt et al. . |
| 5,984,955 | 11/1999 | Wisselink . |
| 5,984,956 | 11/1999 | Tweden et al. . |
| 5,984,963 | 11/1999 | Ryan et al. . |
| 5,984,965 | 11/1999 | Knapp et al. . |
| 5,989,207 | 11/1999 | Hughes . |
| 5,989,287 | 11/1999 | Yang et al. . |
| 5,993,481 | 11/1999 | Marcade et al. . |
| 5,993,482 | 11/1999 | Chuter . |
| 5,997,563 | 12/1999 | Kretzers . |
| 5,997,573 | 12/1999 | Quijano et al. . |
| 6,001,123 | 12/1999 | Lau . |
| 6,004,261 | 12/1999 | Sinofsky et al. . |
| 6,004,347 | 12/1999 | McNamara et al. . |
| 6,004,348 | 12/1999 | Banas et al. . |
| 6,007,575 | 12/1999 | Samuels . |
| 6,007,576 | 12/1999 | McClellan . |
| 6,010,530 | 1/2000 | Goicoechea . |
| 6,017,365 | 1/2000 | Von Oepen . |
| 6,026,814 * | 2/2000 | LaFontaine et al. ................. 128/898 |
| 6,029,672 | 2/2000 | Vanney et al. . |
| 6,035,856 * | 3/2000 | LaFontaine et al. ................. 128/898 |
| 6,045,565 | 4/2000 | Ellis et al. . |
| 6,053,911 | 4/2000 | Ryan et al. . |
| 6,053,924 | 4/2000 | Hussein et al. . |
| 6,053,942 * | 4/2000 | Eno et al. ................. 623/1.15 |
| 6,067,988 | 5/2000 | Mueller . |
| 6,068,638 | 5/2000 | Makower . |
| 6,071,292 | 6/2000 | Makower et al. . |
| 6,076,529 * | 6/2000 | Vanney et al. ................. 128/898 |
| 6,080,163 | 6/2000 | Hussein et al. . |
| 6,093,166 | 7/2000 | Knudson et al. . |
| 6,102,941 | 8/2000 | Tweden et al. . |
| 6,113,630 * | 9/2000 | Vanney et al. ................. 623/1.37 |
| 6,123,682 | 9/2000 | Knudson et al. . |
| 6,126,649 | 10/2000 | Van Tassel et al. . |
| 6,139,541 | 10/2000 | Vanney et al. . |
| 6,152,141 | 11/2000 | Stevens et al. . |
| 6,159,225 | 12/2000 | Makower . |
| 6,162,245 | 12/2000 | Jayaraman . |

FOREIGN PATENT DOCUMENTS

| | | |
|---|---|---|
| 2 316 322 | 2/1998 | (GB) . |
| 94/16629 | 8/1994 | (WO) . |
| 97/13463 | 4/1997 | (WO) . |
| 97/27893 | 8/1997 | (WO) . |
| 97/27896 | 8/1997 | (WO) . |
| 97/27897 | 8/1997 | (WO) . |
| 97/27898 | 8/1997 | (WO) . |
| 97/32551 | 9/1997 | (WO) . |
| 97/41916 | 11/1997 | (WO) . |
| 97/43961 | 11/1997 | (WO) . |
| 98/02099 | 1/1998 | (WO) . |
| 98/06356 | 2/1998 | (WO) . |
| 98/08456 | 3/1998 | (WO) . |
| 98/10714 | 3/1998 | (WO) . |
| 98/16161 | 4/1998 | (WO) . |
| 98/19607 | 5/1998 | (WO) . |
| 98/44869 | 10/1998 | (WO) . |
| 98/46115 | 10/1998 | (WO) . |
| 98/46119 | 10/1998 | (WO) . |
| 98/49964 | 11/1998 | (WO) . |
| 98/53759 | 12/1998 | (WO) . |
| 98/55027 | 12/1998 | (WO) . |
| 98/57591 | 12/1998 | (WO) . |
| 99/08624 | 2/1999 | (WO) . |
| 99/17683 | 4/1999 | (WO) . |
| 99/21490 | 5/1999 | (WO) . |
| 99/21510 | 5/1999 | (WO) . |
| 99/22655 | 5/1999 | (WO) . |
| 99/25273 | 5/1999 | (WO) . |
| 99/32051 | 7/1999 | (WO) . |
| 99/36000 | 7/1999 | (WO) . |
| 99/36001 | 7/1999 | (WO) . |
| 99/37218 | 7/1999 | (WO) . |
| 99/38459 | 8/1999 | (WO) . |
| 99/40868 | 8/1999 | (WO) . |
| 99/47071 | 9/1999 | (WO) . |
| 99/48427 | 9/1999 | (WO) . |
| 99/48545 | 9/1999 | (WO) . |
| 99/49793 | 10/1999 | (WO) . |
| 99/49910 | 10/1999 | (WO) . |
| 99/51162 | 10/1999 | (WO) . |
| 99/53863 | 10/1999 | (WO) . |

| | | |
|---|---|---|
| 99/60941 | 12/1999 | (WO) . |
| 99/62430 | 12/1999 | (WO) . |
| 00/09195 | 2/2000 | (WO) . |
| 00/10623 | 3/2000 | (WO) . |
| 00/12029 | 3/2000 | (WO) . |
| 00/15146 | 3/2000 | (WO) . |
| 00/15148 | 3/2000 | (WO) . |
| 00/15149 | 3/2000 | (WO) . |
| 00/15275 | 3/2000 | (WO) . |
| 0015147 | 3/2000 | (WO) . |
| 00/18325 | 4/2000 | (WO) . |
| 00/18326 | 4/2000 | (WO) . |
| 00/18331 | 4/2000 | (WO) . |
| 00/21436 | 4/2000 | (WO) . |
| 00/21461 | 4/2000 | (WO) . |
| 00/21463 | 4/2000 | (WO) . |
| 00/24449 | 5/2000 | (WO) . |
| 00/33725 | 6/2000 | (WO) . |
| 00/41632 | 7/2000 | (WO) . |
| 00/41633 | 7/2000 | (WO) . |
| 00/45711 | 8/2000 | (WO) . |
| 00/56387 | 9/2000 | (WO) . |
| 00/66035 | 11/2000 | (WO) . |
| 97/13471 | 11/2000 | (WO) . |

OTHER PUBLICATIONS

Zemel, M.D. et al., "Percutaneous Transjugular Portosystemic Shunt," *JAMA*, 1991, vol. 266, No. 3, pp. 390–393.

Massimo, M.D. et al., "Myocardial Revascularization by a New Method of Carrying Blood Directly from the Left Ventricular Cavity into the Coronary Circulation," *Journal of Thoracic Surgeons*, Aug. 1997, vol. 34, No. 2, pp. 257–264.

Lary, M.D. et al., "Myocardial Revascularization Experiments Using the Epicardium," *Archives of Surgery*, Jan. 1969, vol. 98, No. 1, pp. 69–72.

Munro, M.D. et al., "The possibility of myocardial revascularization by creation of a left ventriculocoronary artery fistula," *Journal of Thoracic and Cardiovascular Surgery*, Jul. 1969, vol. 58, No. 1, pp. 25–32.

Kuzela, M.D. et al., "Experimental evaluation fo direct transventricular revascularization," *The Journal of Thoracic and Cardiovascular Surgery*, Jun. 1969, vol. 57, No. 6, pp. 770–773.

Anabtawi, M.D. et al., "Experimental evaluation of myocardial tunnelization as a method of myocardial revascularization," *The Journal of Thoracic and Cardiovascular Surgery*, Nov. 1969, vol. 58, No. 5, pp. 638–646.

Tweden et al., "Ventriculocoronary Artery Bypass (VCAB), a Novel Approach to Myocardial Revascularization," #2000–4653, Feb. 2000.

* cited by examiner

DESIGNS FOR LEFT VENTRICULAR CONDUIT

CROSS-REFERENCE TO RELATED APPLICATIONS

This application claims the benefit of U.S. Provisional Applications Ser. Nos. 60/099,767, filed Sep. 10, 1998, and Ser. No. 60/104,397, filed Oct. 15, 1998.

FIELD OF THE INVENTION

The present invention relates to an apparatus for bypassing a blocked blood vessel segment, and, more particularly, to a conduit or stent positioned between the coronary artery or other blocked vessel and a chamber of the heart, such as the left ventricle of the heart, to bypass a blocked segment of the coronary artery or other blood vessel.

BACKGROUND OF THE INVENTION

Coronary artery disease is a major problem in the U.S. and throughout the world. Coronary arteries as well as other blood vessels frequently become clogged with plaque, which at the very least impairs the efficiency of the heart's pumping action, and can lead to heart attack and death. In some cases, these arteries can be unblocked through noninvasive techniques such as balloon angioplasty. In more difficult cases, a bypass of the blocked vessel is necessary.

In a bypass operation, one or more venous segments are inserted between the aorta and the coronary artery. The inserted venous segments or transplants act as a bypass of the blocked portion of the coronary artery and thus provide for a free or unobstructed flow of blood to the heart. More than 500,000 bypass procedures are performed in the U.S. every year.

Such coronary artery bypass surgery, however, is a very intrusive procedure that is expensive, time-consuming and traumatic to the patient. The operation requires an incision through the patient's sternum (sternotomy), and that the patient be placed on a bypass pump so that the heart can be operated on while not beating. A vein graft is harvested from the patient's leg, another highly invasive procedure, and a delicate surgical procedure is required to piece the bypass graft to the coronary artery (anastomosis). Hospital stays subsequent to the surgery and convalescence are prolonged.

As mentioned above, another conventional treatment is percutaneous transluminal coronary angioplasty (PTCA) or other types of angioplasty. However, such vascular treatments are not always indicated due to the type or location of the blockage, or due to the risk of emboli.

Thus, there is a need for an improved bypass system which is less traumatic to the patient.

SUMMARY OF THE INVENTION

The preferred embodiments of the present invention address the need in the previous technology by providing a bypass system that avoids the sternotomy and other intrusive procedures normally associated with coronary bypass surgery. These embodiments also free the surgeon from the multiple anastomoses necessary in the current process.

The preferred device provides a shunt for diverting blood directly from a chamber in the heart, such as the left ventricle, to the coronary artery, distal to the blockage, therefore bypassing the blocked portion of the vessel. The shunt comprises a stent or conduit adapted to be positioned in the heart wall or myocardium between the left ventricle and the coronary artery that allows for the direct passage of blood therethrough. As used herein, the terms "stent" and "conduit" are interchangeable, and refer to a device that allows for the passage of blood therethrough. The terms "myocardium" and "heart wall" are also used interchangeably. In addition, although the left ventricle is referred to throughout the description, it should be understood that the conduit described herein can be used to provide a passageway for the flow of blood from any heart chamber, not only the left ventricle.

The stent device is delivered either externally or internally through the coronary artery to a position distal to the blockage. At that position, the coronary artery, the myocardium and the wall of the left ventricle are pierced to provide a channel completely through from the coronary artery to the left ventricle of the heart. The stent is then positioned in the channel to provide a permanent passage for blood to flow between the left ventricle of the heart and the coronary artery, distal to the blockage. The stent is sized so that one open end is positioned within the coronary artery, while the other open end is positioned in the left ventricle. The hollow lumen of the stent provides a passage for the flow of blood.

The stent can be self-expandable or expanded by means of a balloon or similar device, and can be provided with various means to anchor it in position within the myocardium, such as expandable legs, hooks, barbs, collars, suture holes and the like. The stent can be formed from a plurality of rings, which can be connected to provide stability. The stent can include a valve in its interior, and can also be used to deliver drugs or other pharmaceutical compounds directly into the myocardium and the coronary circulation.

DETAILED DESCRIPTION OF THE PREFERRED EMBODIMENT

Figure 1A:
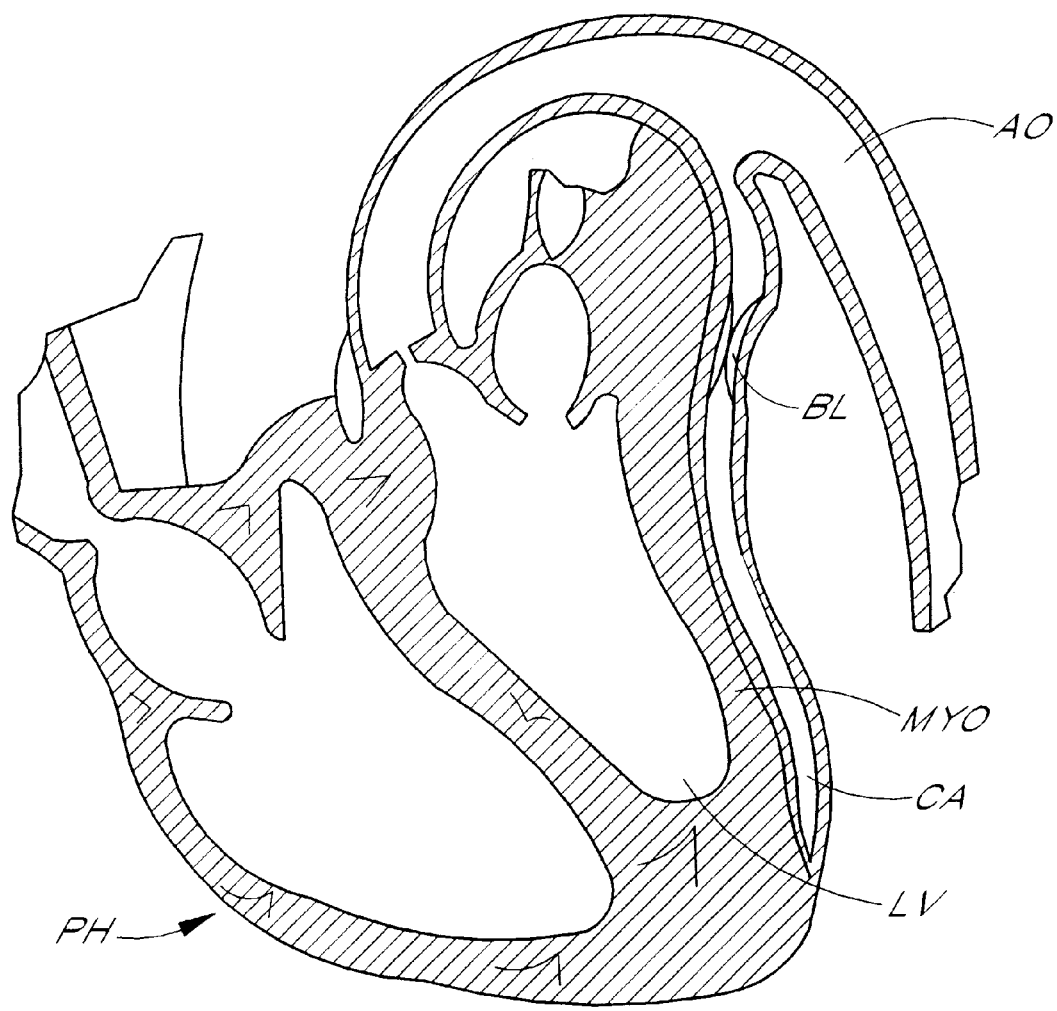
FIG. 1A is a cross-sectional view of a human heart, aorta and coronary artery.

As is well known, the coronary artery branches off the aorta and is positioned along the external surface of the heart wall. The anatomy of the human heart is illustrated in FIG. 1A. Oxygenated blood flows from the heart PH to the aorta AO, on to the rest of the body, some of the blood flowing into the coronary artery CA. In some individuals, plaque builds up within the coronary artery CA, blocking the free flow of blood and causing complications ranging from mild angina to heart attack and death.

In order to restore the flow of oxygenated blood through the coronary artery, one embodiment of the present invention provides for the shunting of blood directly from the heart to a site in the coronary artery that is distal to the blockage. A channel is formed through the wall of the coronary artery and the myocardium and into the left ventricle of the heart that lies beneath the coronary artery. A stent or conduit is positioned in the passage to keep it open, and allow for the flow of oxygenated blood directly from the heart into the coronary artery. Again, it should be understood that while the insertion of the conduit in the myocardium between the left ventricle and the coronary artery is described in detail below, this is merely exemplary and use of the conduit between other chambers of the heart and the coronary artery, and between blood vessels is also contemplated.

The principles of the present invention are not limited to left ventricular conduits, and include conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. For example, in one preferred embodiment of the present invention, the conduit communicates from the left ventricle, through the myocardium, into the pericardial space, and then into the coronary artery. However, other preferred embodiments are disclosed, including direct transmyocardial communication from a left ventricle, through the myocardium and into the coronary artery. Thus, as emphasized above, the term "transmyocardial" should not be narrowly construed in connection with the preferred fluid communication conduits, and other non-myocardial and even noncardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the occlusions which are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Moreover, the conduits are not necessarily stented or lined with a device but can comprise mere tunnels or openings formed in the tissues of the patient.

The conduits of the present invention preferably comprise both integral or one-piece conduits as well as plural sections joined together to form a continuous conduit. The present conduits can be deployed in a variety of methods consistent with sound medical practice including vascular or surgical deliveries, including minimally invasive techniques. For example, various preferred embodiments of delivery rods and associated methods may be used. In one embodiment, the delivery rod is solid and trocar-like. It may be rigid or semi-rigid and capable of penetrating the tissues of the patient and thereby form the conduit, in whole or in part, for purposes of fluid communication. In other preferred embodiments, the delivery rods may be hollow so as to form the conduits themselves (e.g., the conduits are preferably self-implanting or self-inserting) or have a conduit mounted thereon (e.g., the delivery rod is preferably withdrawn leaving the conduit installed). Thus, the preferred conduit device and method for installation is preferably determined by appropriate patient indications in accordance with sound medical practices.

In some individuals, aortic insufficiency or peripheral venous insufficiency occurs. Aortic insufficiency is the leakage of blood through the aortic valve, resulting in a backflow of blood into the left ventricle. The heart compensates for the backflow of blood by pumping harder, resulting in hypertrophy (thickening of the heart muscle) and dilation of the left ventricle wall. Left untreated, heart failure can result. In venous insufficiency, the heart valves are unable to prevent the backflow of blood. This too can result in heart failure. Accordingly, one embodiment of the invention provides for the use of a conduit placed within the heart wall to improve the flow of oxygenated blood through the body.

Figure 1B:
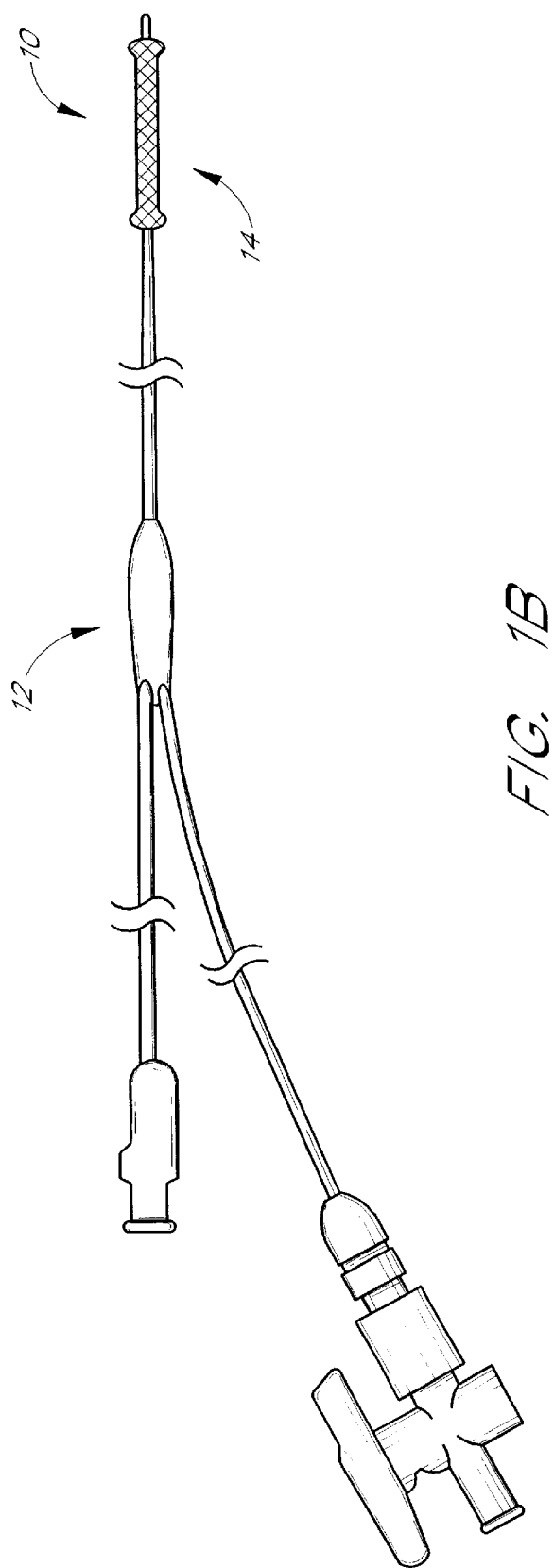
FIG. 1B is a side view of one embodiment of an expandable stent and the balloon catheter used for stent delivery.
Figure 2:
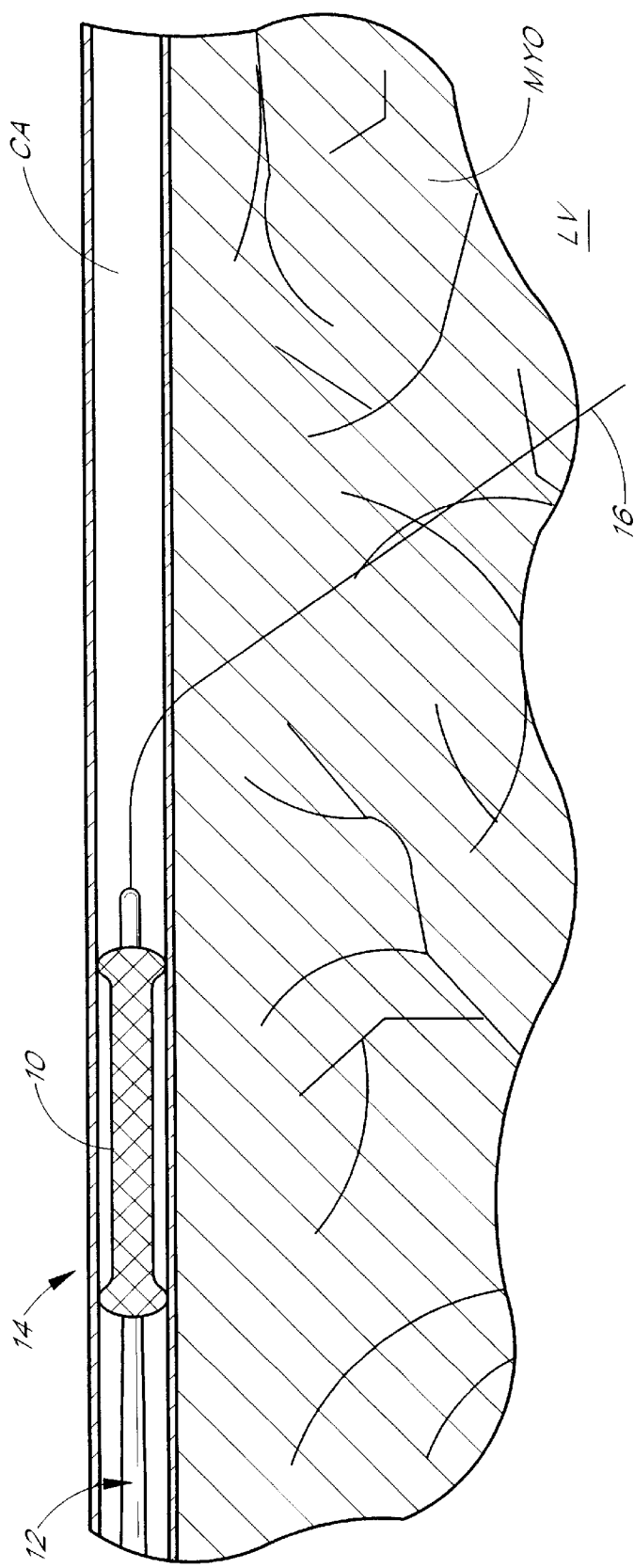
FIG. 2 is a side view of the stent of FIG. 1B mounted on the distal end of the catheter for delivery into the myocardium, with the coronary artery and myocardium shown cut-away.

A first embodiment of the present invention is illustrated in FIG. 1B. This embodiment is a balloon-expanded stent 10. The stent 10 is introduced as described below, using a high-pressure balloon catheter 12 to deploy the stent 10 once it is properly positioned in the myocardium MYO (FIG. 2). When the stent 10 is positioned inside the myocardial wall MYO, the balloon 14 is inflated to expand the stent 10 and open the conduit from the left ventricle LV into the coronary artery CA. The stent 10 can include attachment mechanisms not limited to hooks, barbs, flanges, large collars, suture holes and/or other means to ensure a seal is created between the coronary artery CA and the wall of the myocardium MYO and to prevent the threat of stent 10 migration. When the attachment of the stent 10 is completed, the remaining catheter assembly 12 is removed, leaving the stent 10 in place. Upon deflating the balloon 14, the stent 10 will remain open. Because of the shape of this stent 10, a dumbbell shaped balloon 14 is preferably used to ensure proper expansion, as described below.

FIGS. 1B through 4 illustrate the introduction of the balloon-expanded stent 10 into the myocardial wall MYO. FIG. 1B illustrates the stent 10 mounted over the balloon 14 on the distal end of the stent introducer catheter 12. FIG. 2 illustrates the stent introducer catheter 12 following the path created by a puncture wire 16 extending past the distal end-of the introducer catheter 12, and used to access the left ventricle LV through the coronary artery CA and myocardium MYO. Further details regarding conduits and conduit delivery systems are described in copending patent applications entitled DELIVERY METHODS FOR LEFT VENTRICULAR CONDUIT Ser. No. 09/368,868, LEFT VENTRICULAR CONDUIT WITH BLOOD VESSEL GRAFT, VALVE DESIGNS FOR LEFT VENTRICULAR CONDUIT Ser. No. 09/368,393, LEFT VENTRICULAR CONDUITS TO CORONARY ARTERIES AND METHODS FOR CORONARY BYPASS Ser. No. 09/534,038, and BLOOD FLOW CONDUIT DELIVERY SYSTEM AND METHOD OF USE Ser. No. 09/368,644, all filed on the same day as the present application, and U.S. Pat. Nos. 5,429,144 and 5,662,124, the disclosures of which are all hereby incorporated by reference in their entirety.

Figure 3:
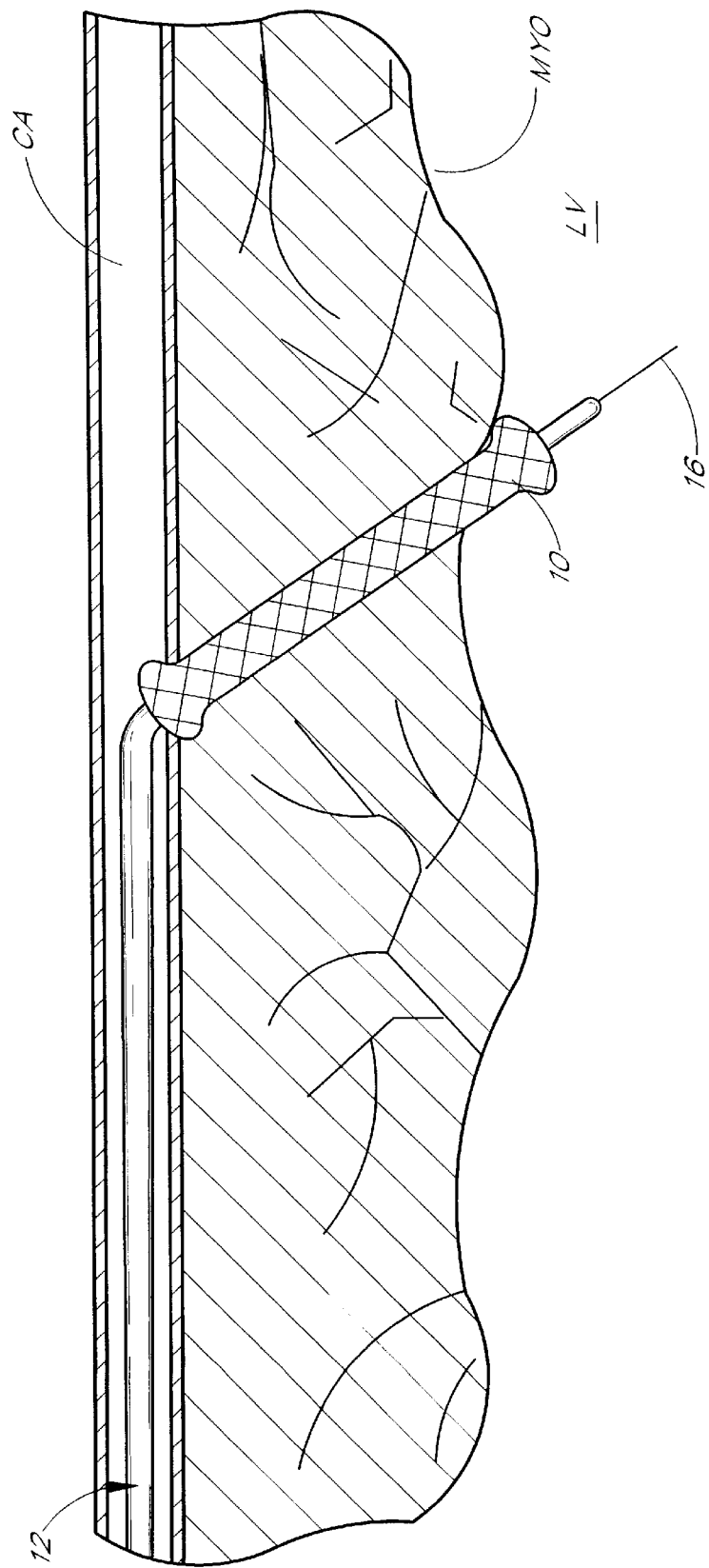
FIG. 3 is a side view of the distal end of the stent/catheter assembly of FIG. 1B positioned in the myocardium, with the coronary artery and myocardium shown cut-away.
Figure 4:
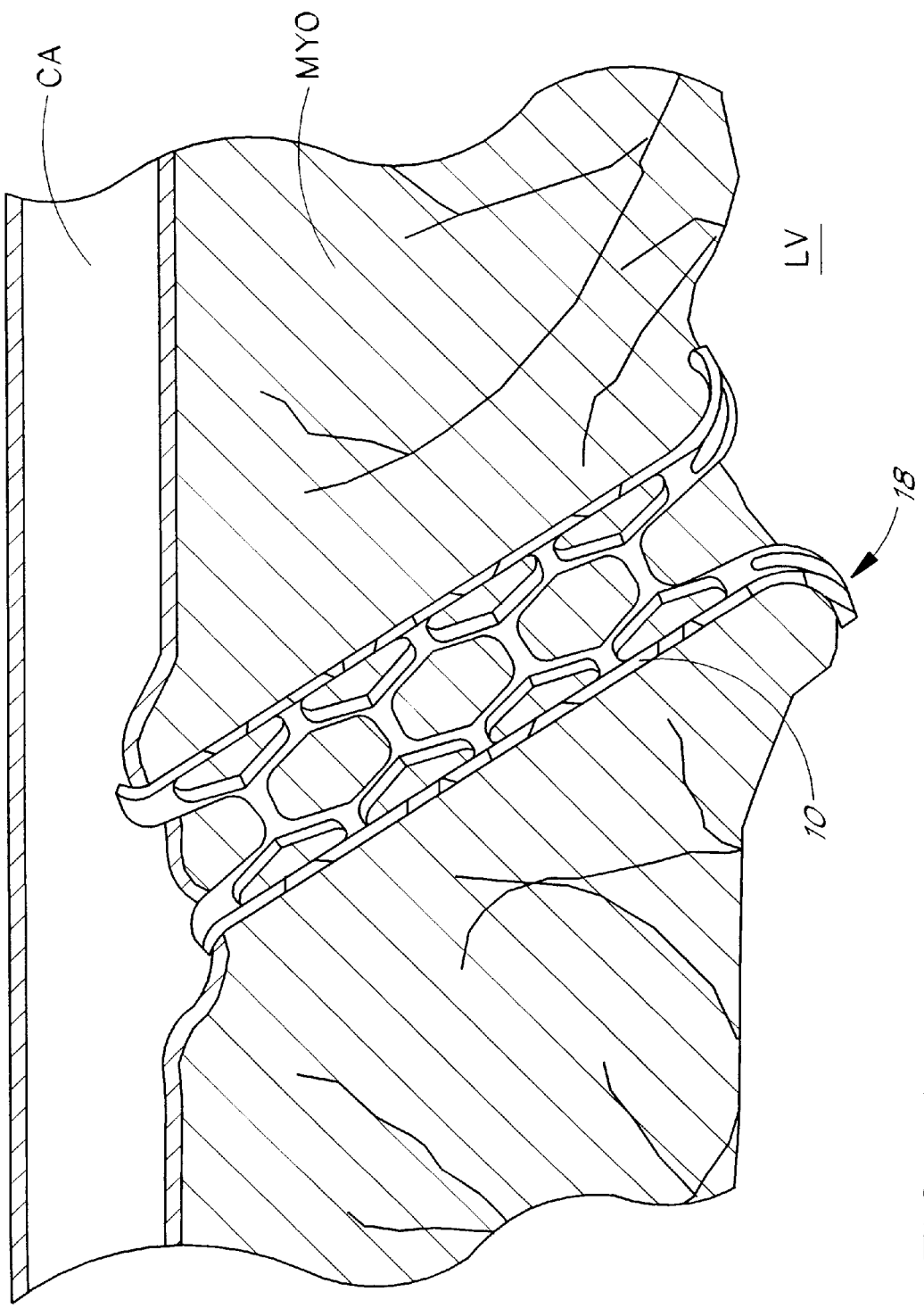
FIG. 4 is a cross-sectional side view of the stent of FIG. 1B positioned within the myocardium after removal of the catheter used for delivery.

FIG. 3 illustrates the non-expanded stent 10 positioned inside the myocardial wall MYO prior to inflation of the balloon 14. FIG. 4 illustrates an expanded stent 10 in position, with the introducer catheter 12 removed. Because of the way the attachment mechanisms 18 expand on this stent 10, a dumbbell shaped balloon 14 is preferably used to flare out the ends of the stent 10. These flared edges 18 maintain the stent 10 in its proper position in the heart wall MYO and provide a seal between the coronary artery CA and the outer heart wall MYO.

The second embodiment of the stent or conduit incorporates a self-expanding stent 20, illustrated in FIGS. 5–8. The stent 20, having a retaining sheath 26 to hold it in a non-expanded configuration, is introduced into the wall of the myocardium MYO as follows. The stent delivery catheter 22 is advanced over a puncture mechanism 24 and into the wall of the myocardium MYO as described above. When the stent 20 is properly seated in the myocardial wall MYO, its retaining sheath 26 is withdrawn, allowing the stent 20 to expand and open a conduit from the ventricle LV to the coronary artery CA. This stent 20 also includes attachment mechanisms not limited to hooks, barbs, flanges, large collars, suture holes and/or other means to ensure a seal is created between the artery CA and the wall of the myocardium MYO, and to prevent the threat of stent 20 migration. When the positioning is completed, the remaining catheter assembly 22 is removed, leaving the stent 20 in place.

Figure 5:
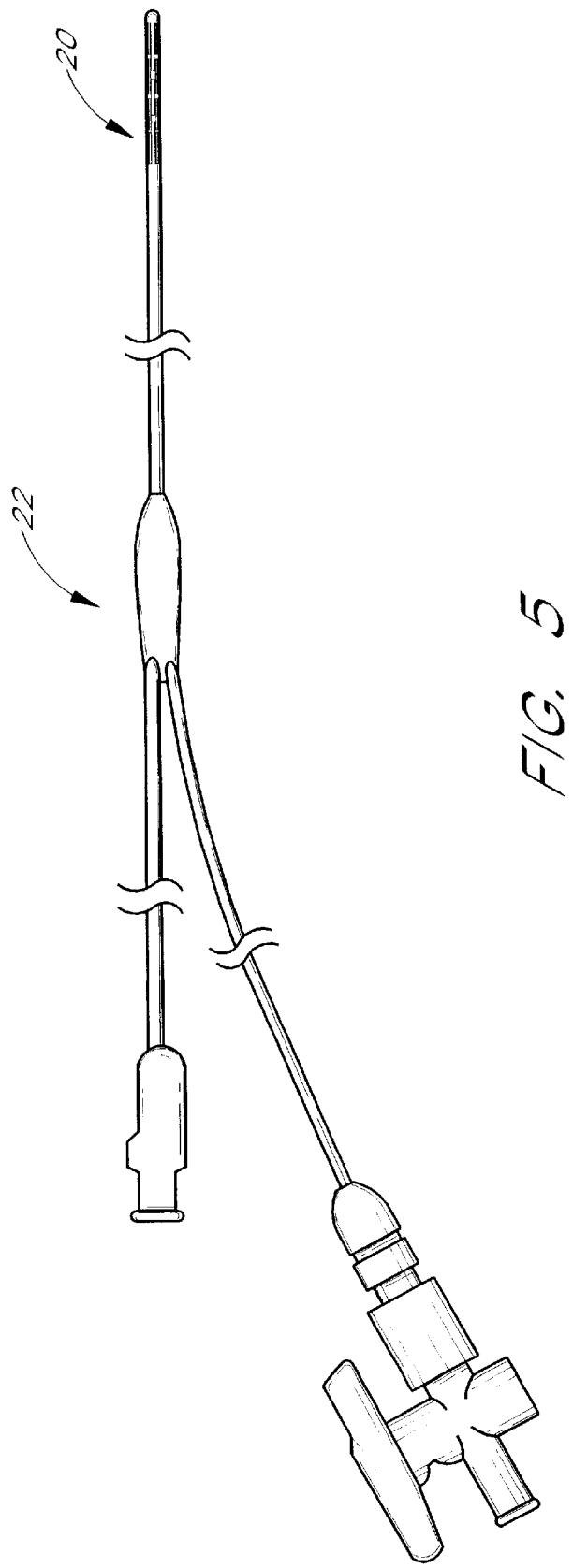
FIG. 5 is a side view of another embodiment of the stent and the catheter used for stent delivery.
Figure 6:
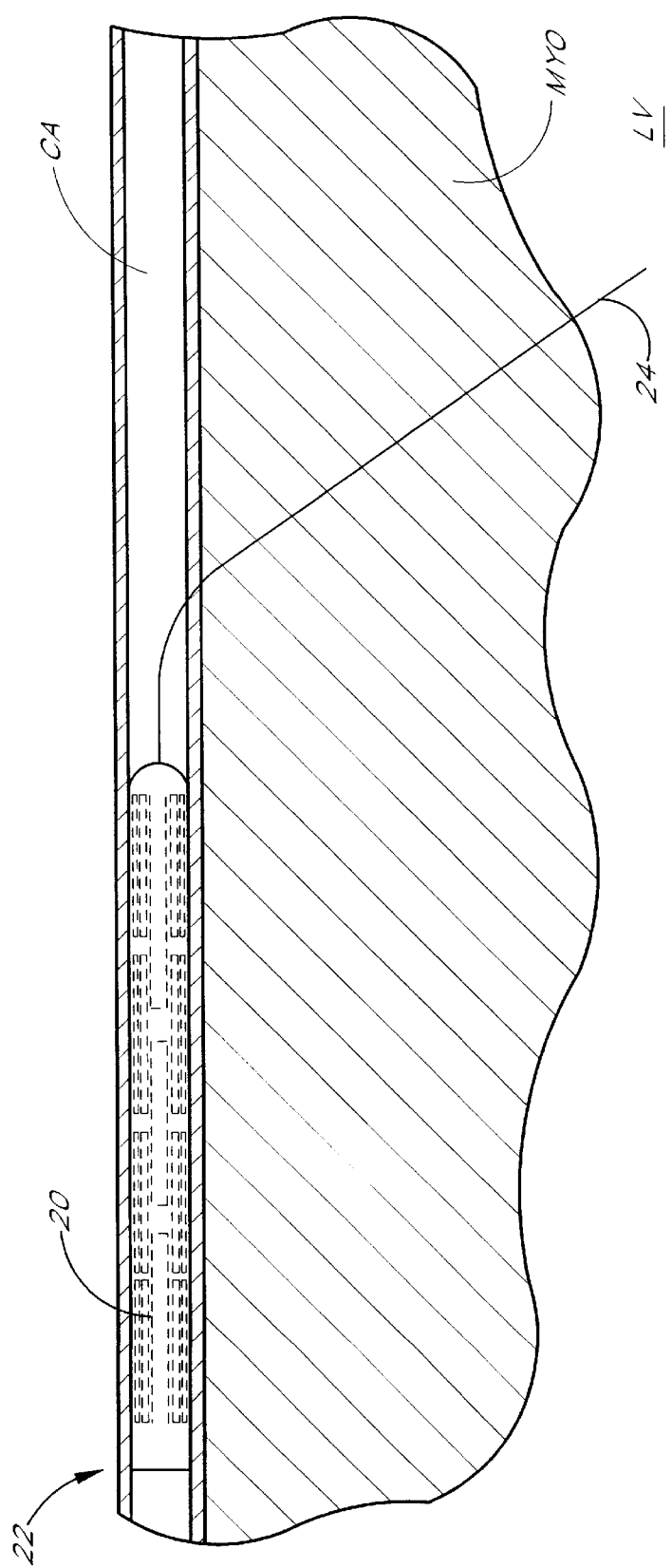
FIG. 6 is a cross-sectional side view of the catheter and puncture device used to introduce the self-expanding stent of FIG. 5 into the myocardium.
Figure 7:
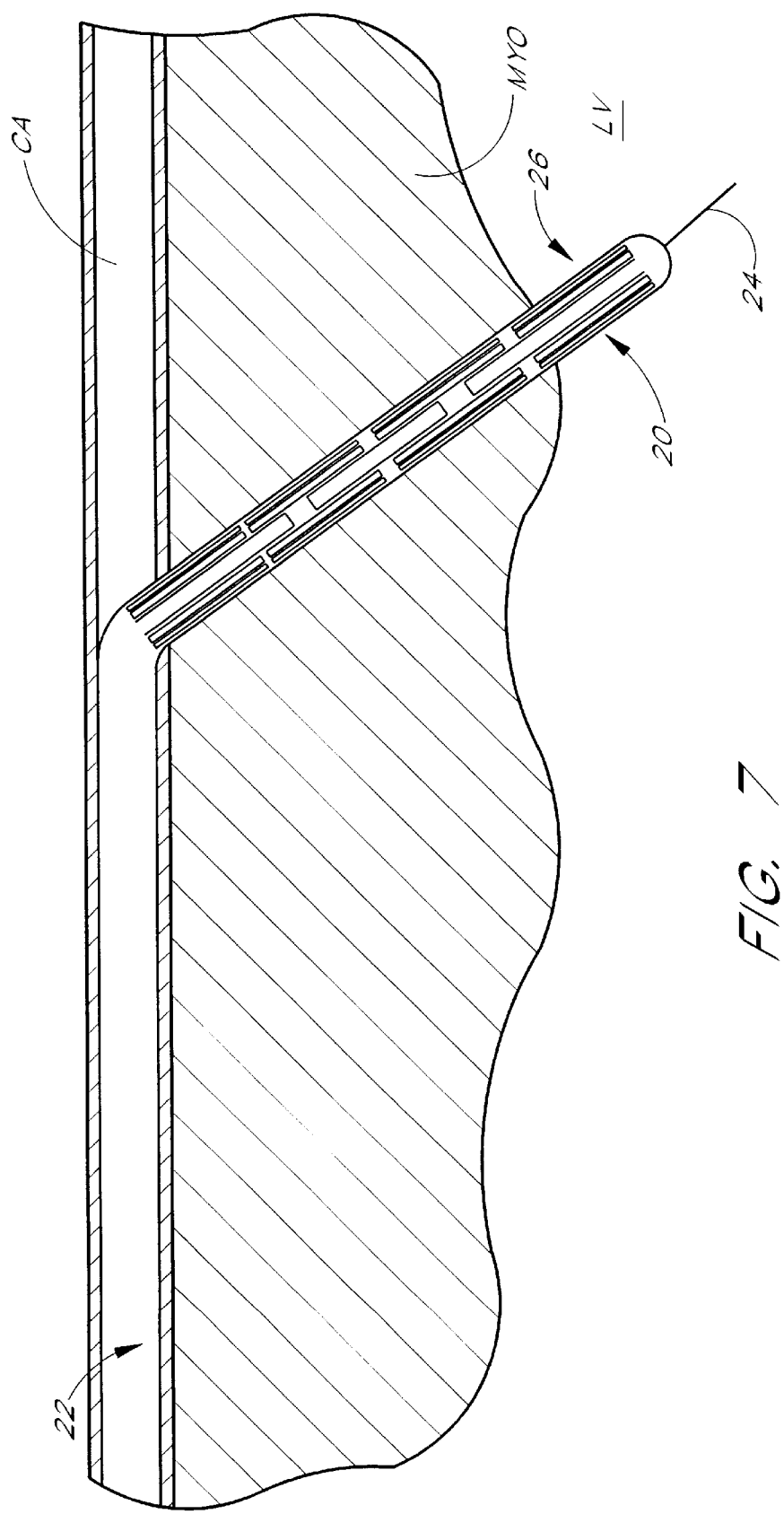
FIG. 7 is a cross-sectional side view of the stent/catheter assembly of FIG. 5 positioned in the myocardium.
Figure 8:
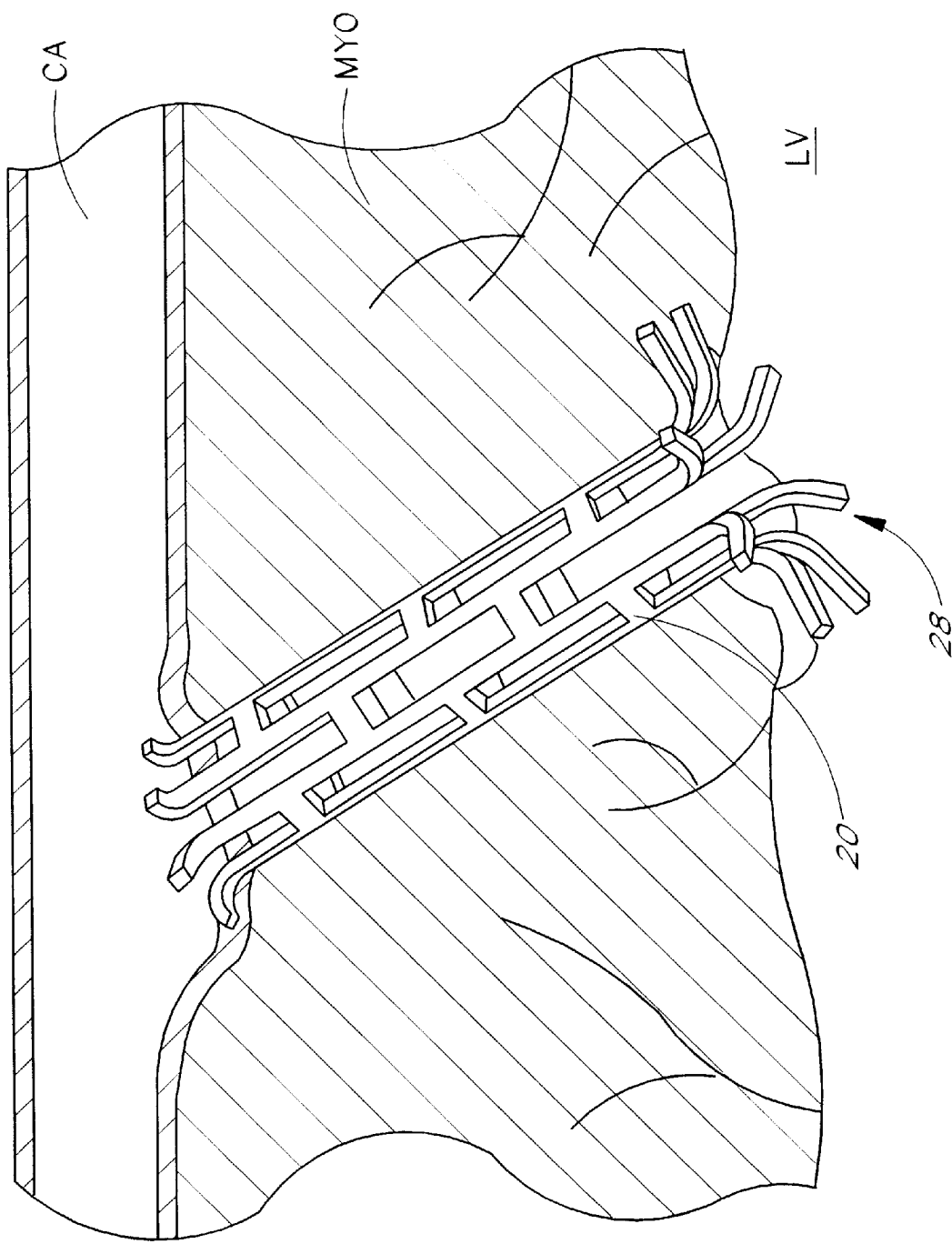
FIG. 8 is a side view of the self-expanding stent of FIG. 5 positioned within the myocardium after removal of the catheter and puncture device, with the coronary artery and myocardium shown cut-away.

The self-expanding stent 20 mounted on the distal end of the stent introducer catheter 22 is illustrated in FIG. 5. FIG. 6 illustrates the stent introducer 22 following the path created by a puncture wire 24 used to form the passage between the coronary artery CA and the left ventricle LV. FIG. 7 illustrates a non-expanded stent 20 located in position on the stent introducer catheter 22 with the introducer catheter 22 in position in the heart wall MYO. FIG. 8 illustrates the self-expanding stent 20 in position, with the introducing catheter 22 removed. Flared edges 28 on the stent 20 maintain its proper position in the heart wall MYO and provide a seal between the coronary vessel CA and outer surface of the heart MYO.

For the stent designs described above, additional anchoring methods may be desired to maintain the stent's proper position and/or create a leak-free seal in the coronary artery. Suitable attachment mechanisms include a set of barbs located on the stent body or flares and a collar on the coronary side to help seal and prevent blood from exiting the gap between the vessel and outer heart wall. The stent can also be anchored in place by applying sutures. The stent can include holes at either end to facilitate the placement of these anchoring sutures. A suture gun can be used to apply multiple sutures at the same time. In addition, the stents can be lined, if desired, with materials such as polymers, for example polytetrafluoroethylene (PTFE), silicone or GORTEX, to provide for the ease of blood flow therethrough.

Figure 9:
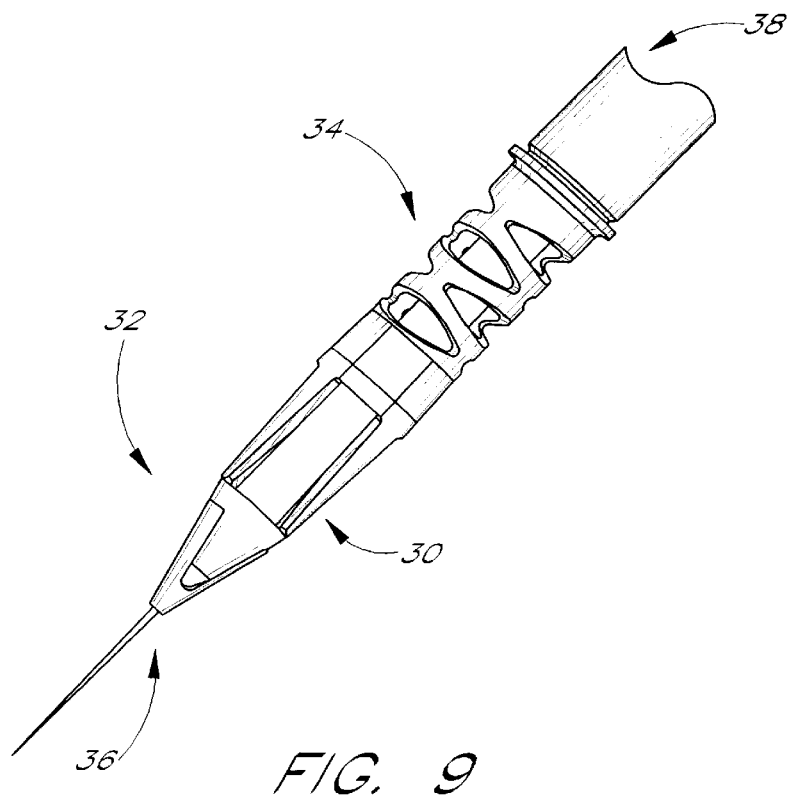
FIG. 9 is a perspective view of another embodiment of the stent having expandable legs, showing the stent mounted on the distal end of the introducer catheter.
Figure 10:
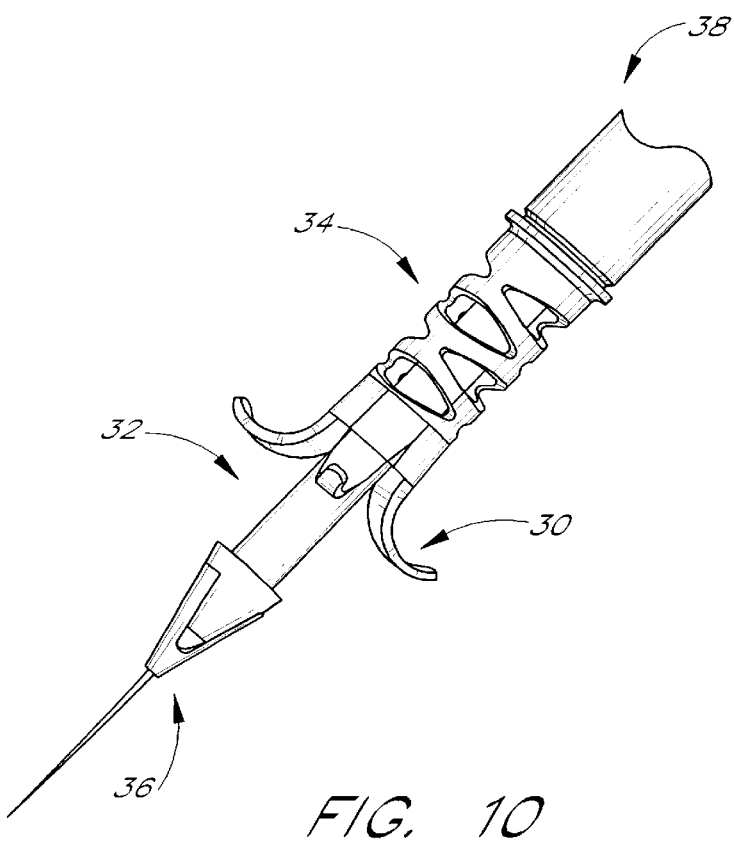
FIG. 10 is a perspective view of the stent of FIG. 9, showing the distal end of the introducer catheter pushed forward to allow the legs of the stent to expand.
Figure 11:
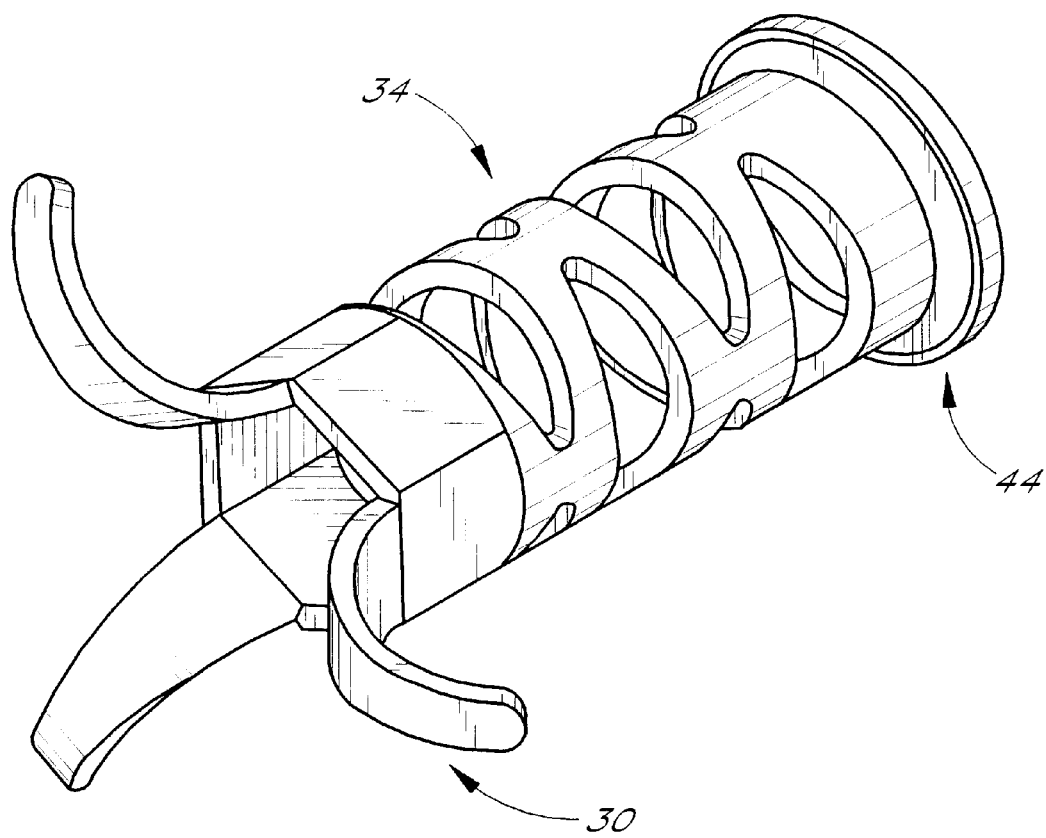
FIG. 11 is a perspective view of the stent of FIG. 9, showing the legs of the stent in an expanded position.

A third embodiment of the stent design, illustrated in FIGS. 9-11, incorporates attachment flanges or "legs" 30 that expand after introduction into the myocardium to hold the stent 34 in place. The puncture instrument 32 and stent 34 are mated together and are advanced into the myocardial wall as a single unit. The puncture instrument's distal end 36 is shaped in a "nose-cone" configuration, which is responsible for containing the legs 30 of the stent 34 while it is being introduced into the wall of the myocardium. When the stent 34 is in the proper position in the myocardial wall, the nose cone 36 is pushed forward, releasing the attachment legs 30 of the stent 34. The internal diameter (ID) of the stent 34 is large enough to allow the nose cone 36 to pass back through. The stent 34 is then released from the catheter 38 and the catheter 38 is removed.

FIG. 9 illustrates the stent 34 mounted on the introducer catheter 38. The expanding legs 30 of the stent 34 are held in place by the nose cone 36 on the distal end of the catheter 38 that acts as a dilator. The catheter assembly 38 is advanced over a puncture wire if desired, into proper position in the myocardium, and the nose cone 36 is pushed forward allowing the legs 30 to expand as shown in FIG. 10. The nosecone/puncture assembly 32, 36 is then withdrawn through the lumen of the stent 34. When the nose-cone/puncture assembly 32, 36 is removed, the stent 34 can be pushed off the introducer catheter 38 and remains in the myocardium in the position shown in FIG. 11. FIG. 11 also illustrates a sealing collar 44 that may be used in the interface between the coronary artery and the outer wall of the heart to prevent hemorrhaging around the stent 34 and to hold the stent 34 in place. Sutures can be used to ensure that the stent is maintained in its proper position and prevent migration.

Figure 12:
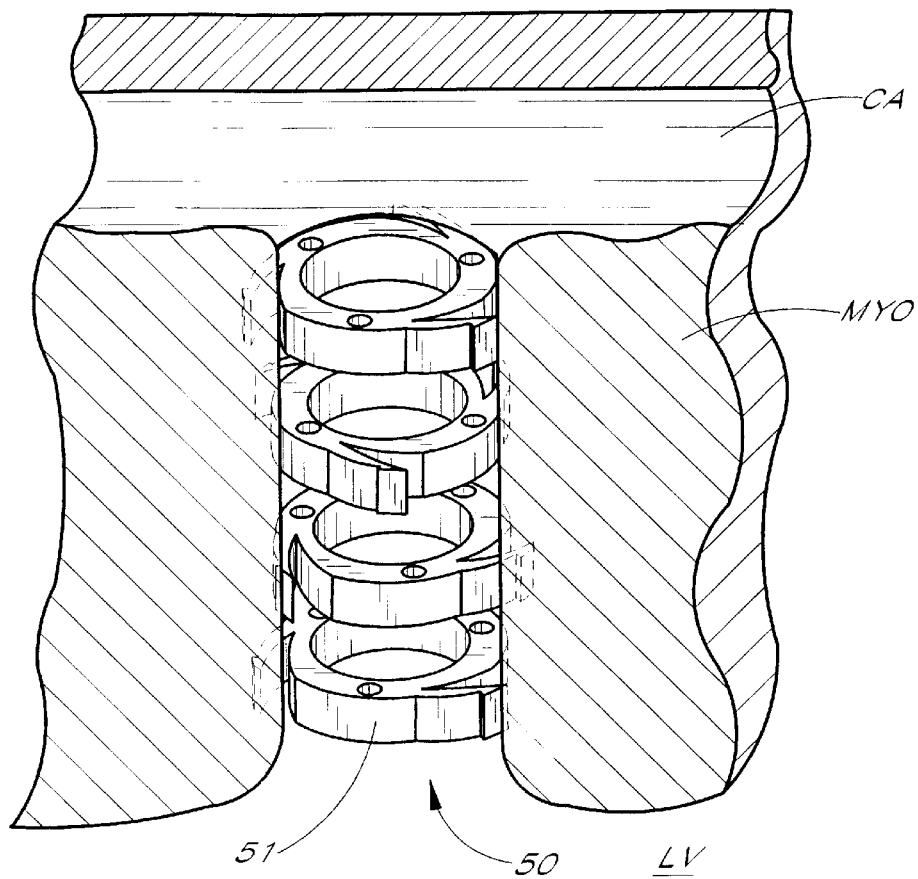
FIG. 12 is a side view of another embodiment of the stent positioned within the myocardium, with the coronary artery and myocardium shown cut-away.

FIG. 12 illustrates a further embodiment of the present invention, a "bulkhead" stent 50. This stent 50 consists of a plurality of rings, which are placed in the myocardium MYO. The rings 50 form a passage through which blood flows from a chamber in the heart, such as the left ventricle LV, directly into the coronary artery CA. The stent 50 is preferably formed of biocompatible material such as a metal or polymer. A gun or other suitable device can be used to implant the stent 50 in the myocardium MYO.

If desired, the separate units or rings of the stent 50 can be connected via a wire, suture thread, or similar means. The wire is threaded through the holes 51 located in each ring. Connecting the rings of the stent 50 in this manner serves to make the stent 50 more stable and to prevent the migration of the individual units. If desired, a valve (not shown) can be incorporated into the stent 50 to help prevent the backflow of blood into the left ventricle LV. Additional details regarding valve designs are disclosed in the above referenced copending applications entitled LEFT VENTRICULAR CONDUIT WITH BLOOD VESSEL GRAFT, VALVE DESIGNS FOR LEFT VENTRICULAR CONDUIT Ser. No. 09/368,868 and LEFT VENTRICULAR CONDUITS TO CORONARY ARTERIES AND METHODS FOR CORONARY BYPASS Ser. No. 09/534,038, filed on the same day as the present application, all of which are incorporated by reference in their entirety.

Figure 13:
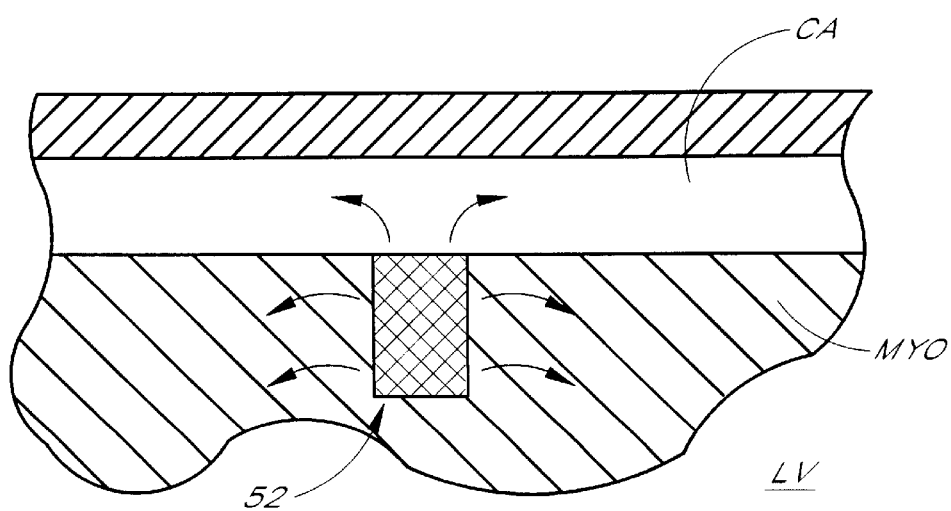
FIG. 13 is a side view of a biodegradable stent positioned within the myocardium, with the coronary artery and myocardium shown cut-away.

If desired, the stent or conduit of the present invention can be formed of biodegradable or bioabsorbable materials and/or used to deliver drugs directly into the myocardium and the coronary circulation. Such a stent 52 is illustrated in FIG. 13. The biodegradable stent 52 can extend only partially through the myocardium MYO as illustrated in FIG. 13, but can also extend entirely through from the left ventricle LV to the coronary artery CA. Once positioned in the myocardium MYO, the stent 52 degrades, dissolves or is absorbed over time to release drugs, genes, angiogenesis or growth factors, or other pharmaceutical compounds directly into the heart muscle MYO and the coronary artery CA, as shown by the arrows in FIG. 13. Bioabsorbable materials include, but are not limited to, polymers of the linear aliphatic polyester and glycolide families, such as polylactide and polyglycolide. Further details are described in the above-referenced application entitled LEFT VENTRICULAR CONDUITS TO CORONARY ARTERIES AND METHODS FOR CORONARY BYPASS Ser. No. 09/534,038, filed on the same date as the present application.

Figure 14:
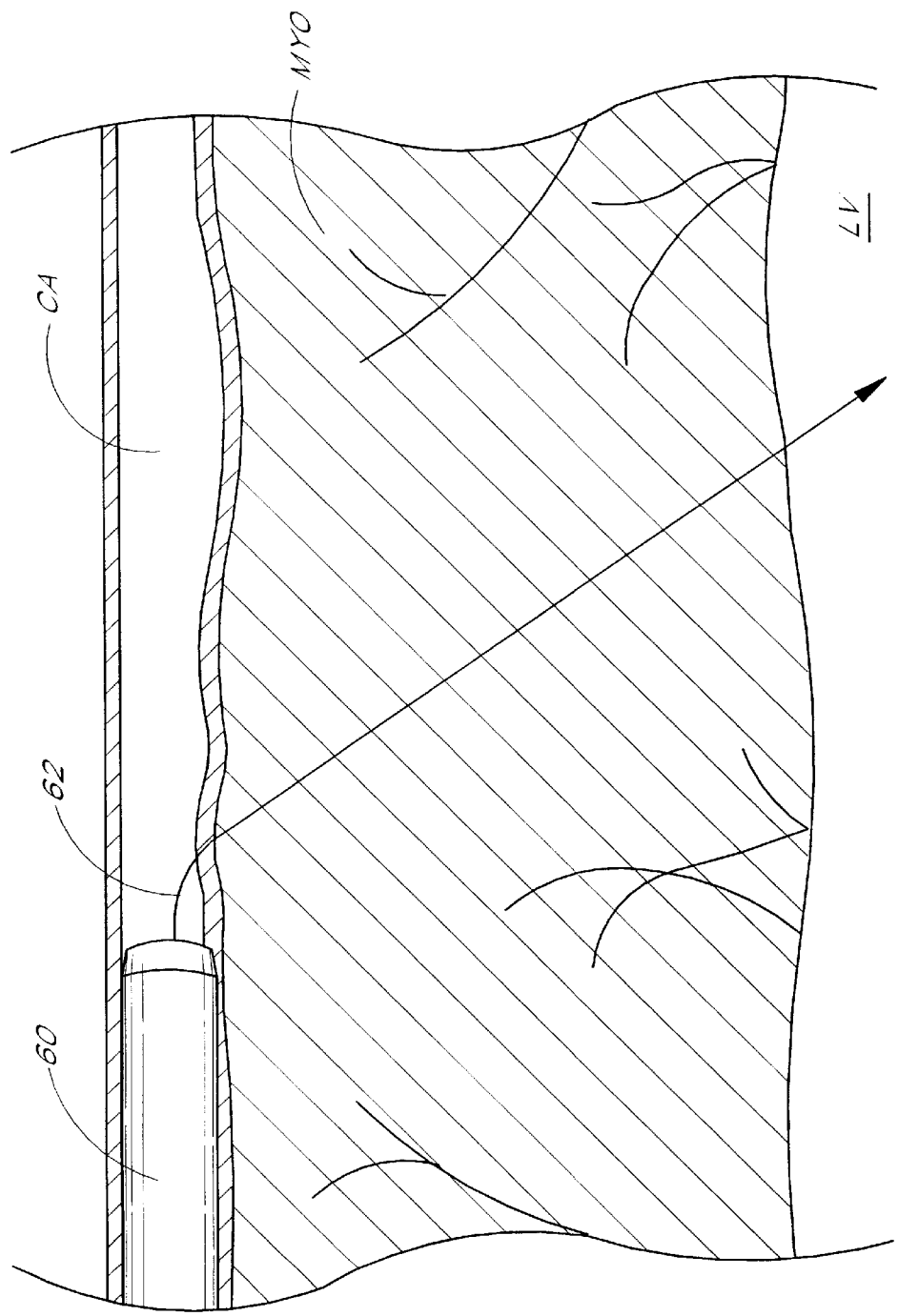
FIG. 14 is a side view of a catheter and puncture device used to introduce a bulkhead stent into the myocardium, with the coronary artery and myocardium shown cut-away.
Figure 15:
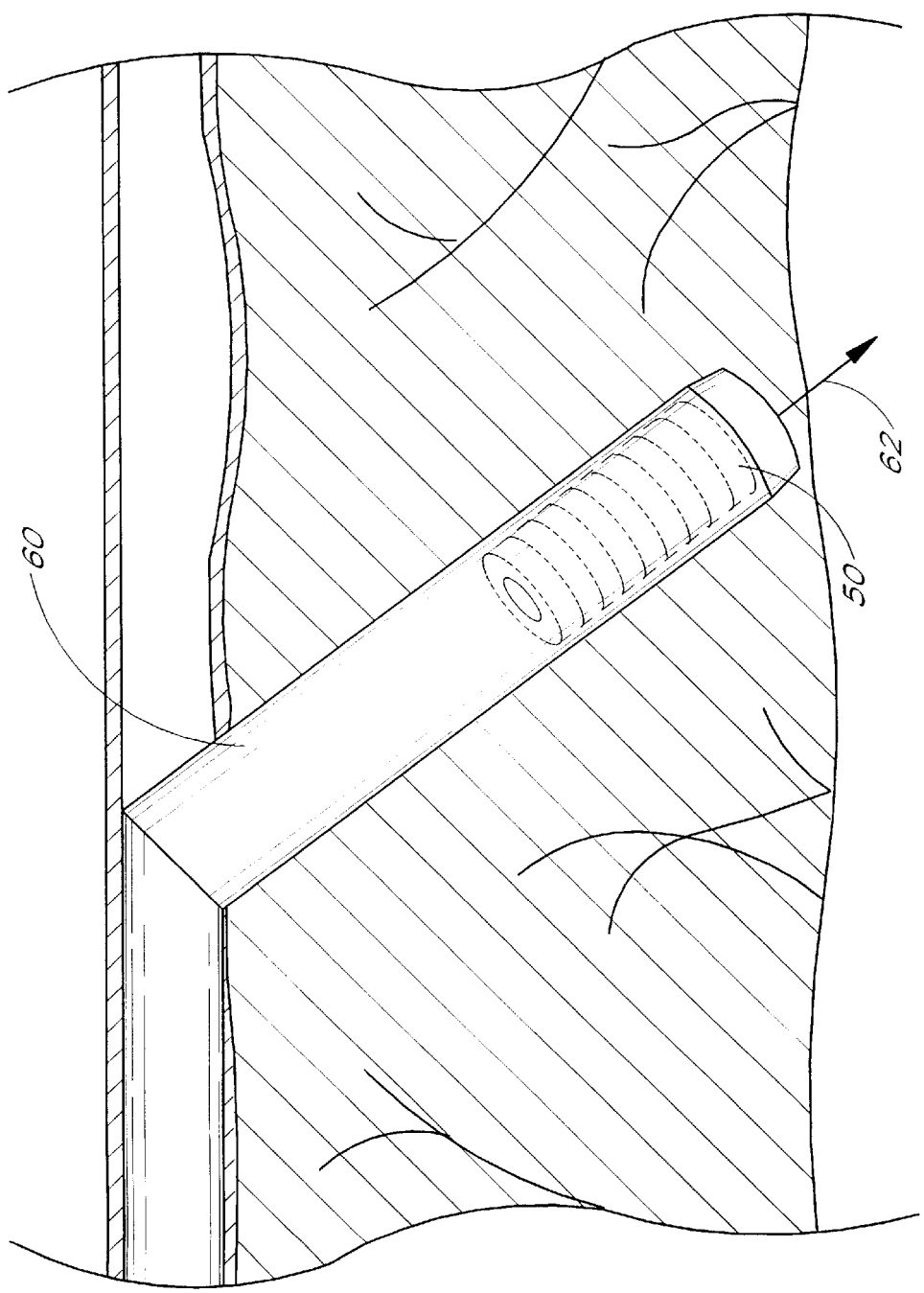
FIG. 15 is a side view of the stent/catheter assembly of FIG. 14 positioned in the myocardium, with the coronary artery and myocardium shown cutaway.
Figure 16:
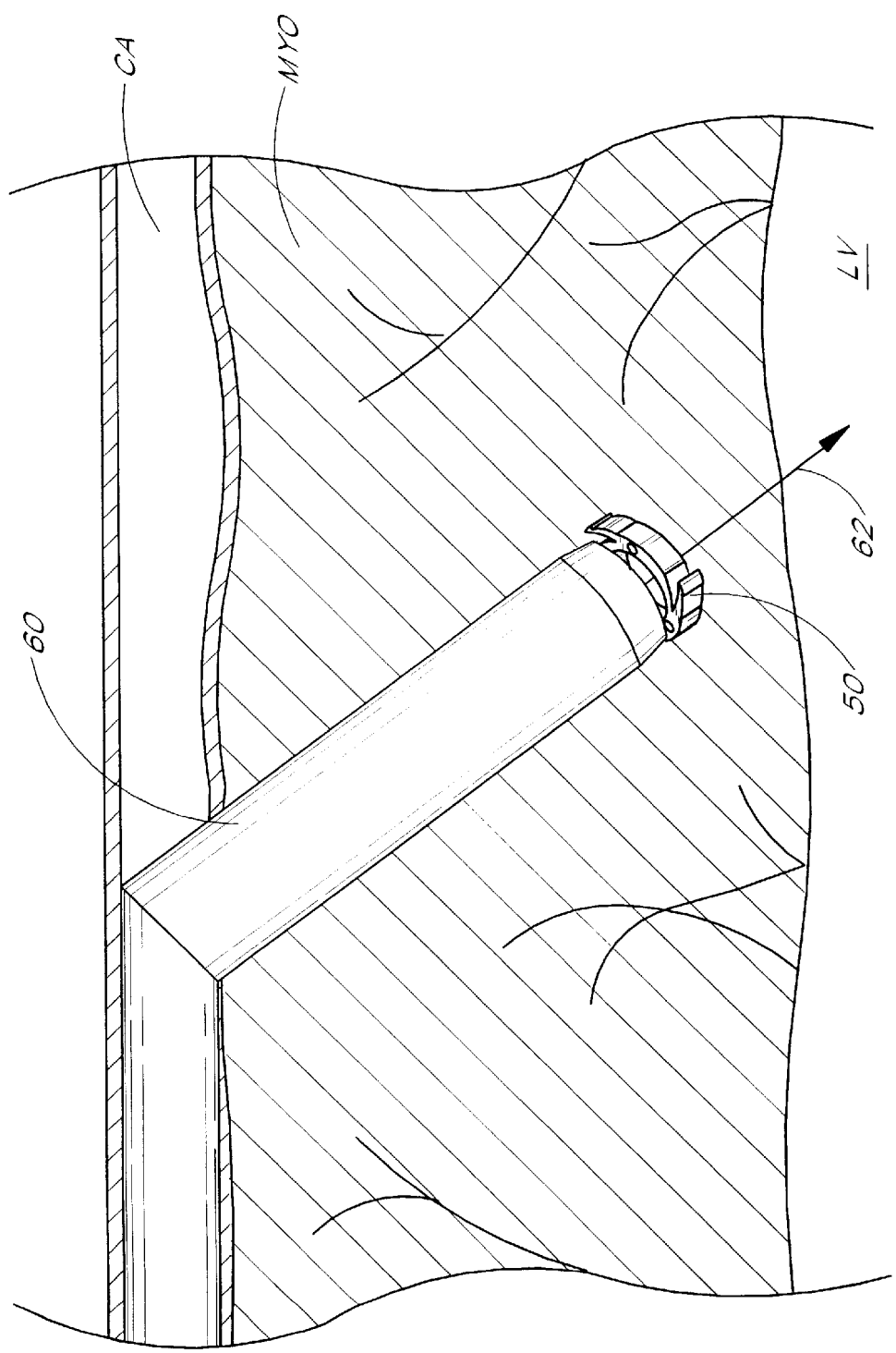
FIGS. 16–19 are progressive side views of the stent/catheter assembly of FIG. 14, showing the bulkhead stent being deployed into the myocardium.
Figure 17:
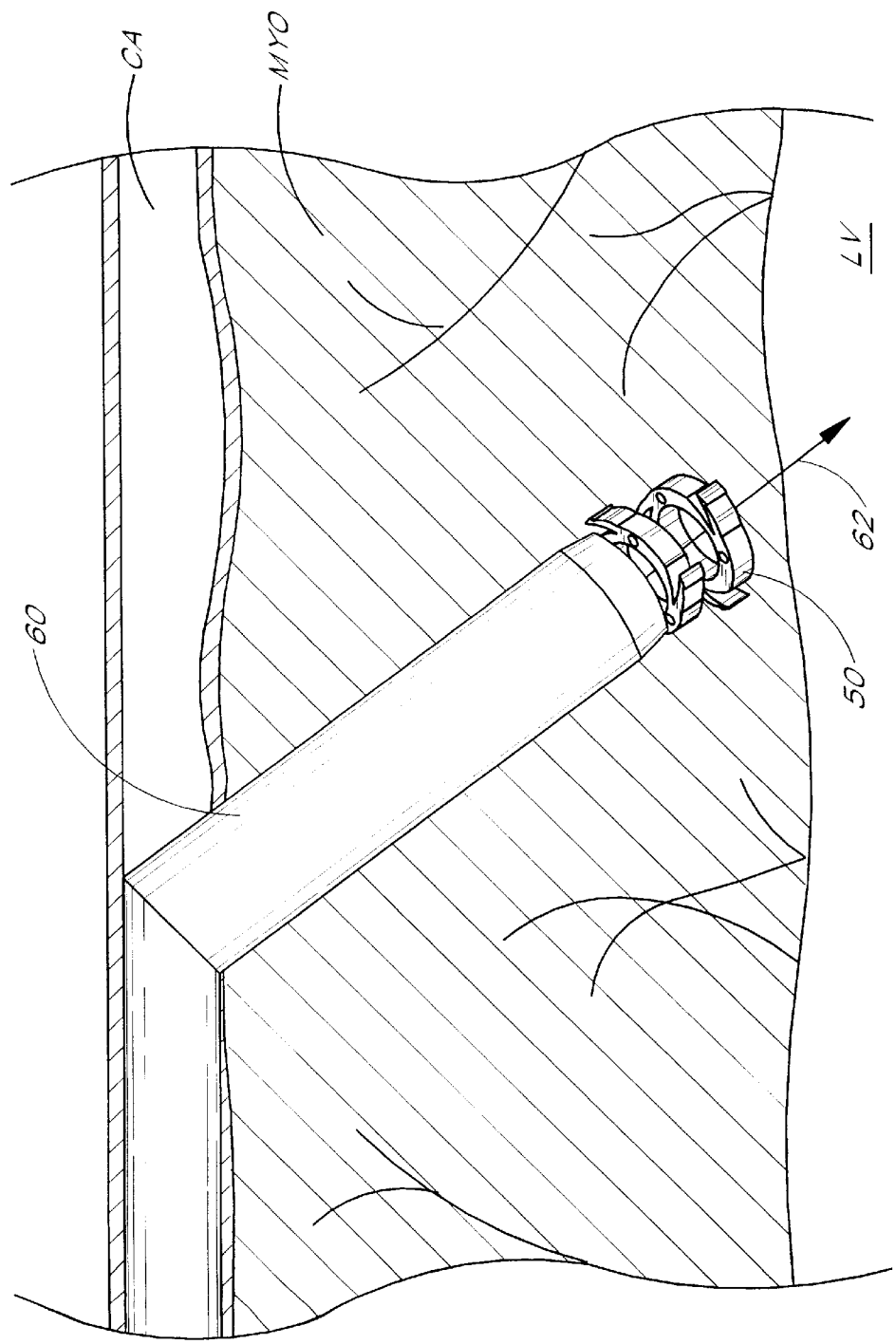
Figure 18:
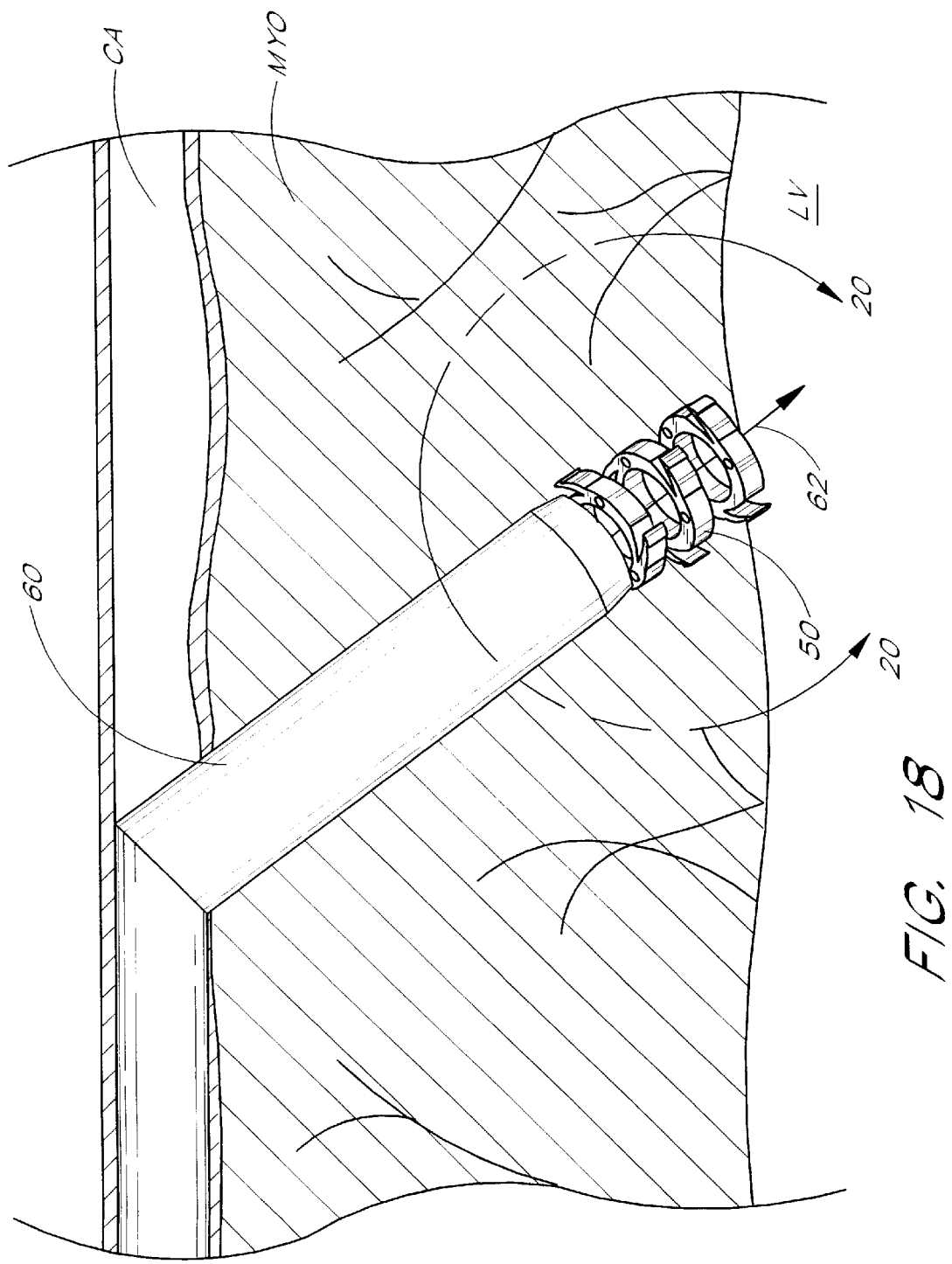
Figure 19:
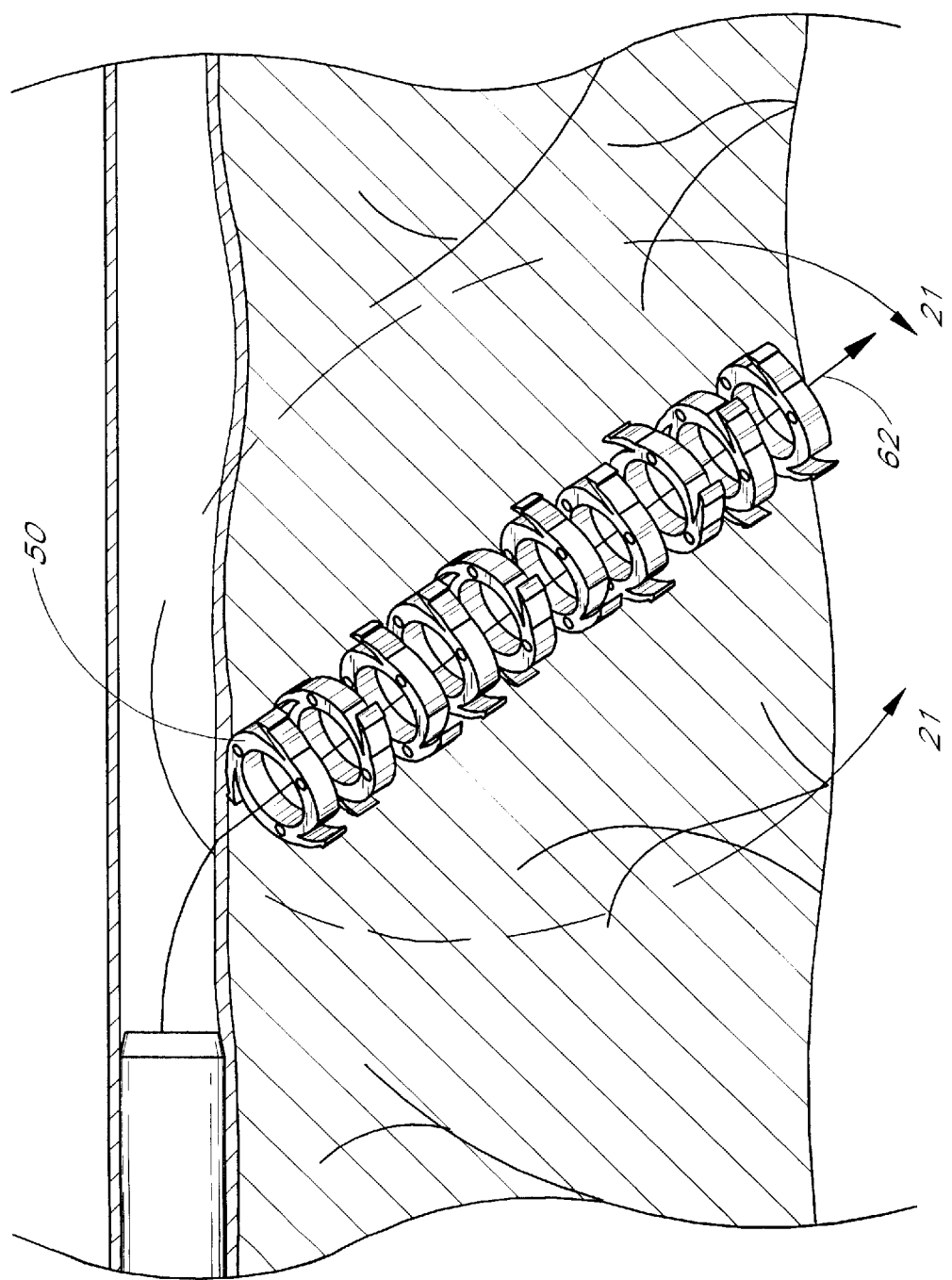
Figure 20:
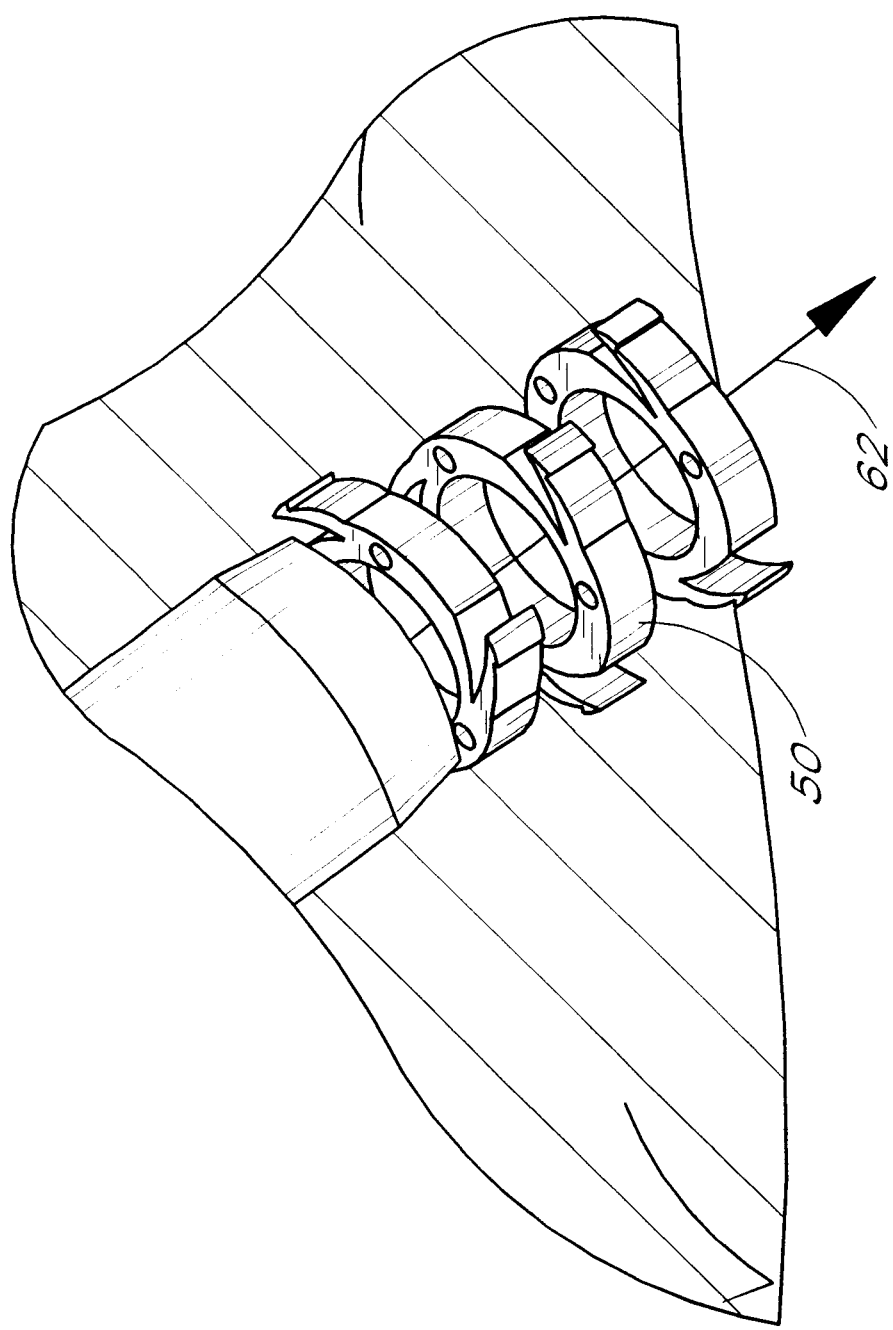
FIGS. 20 and 21 are enlarged views of FIGS. 18 and 19, respectively, showing the bulkhead stent being deployed into the myocardium.
Figure 21:
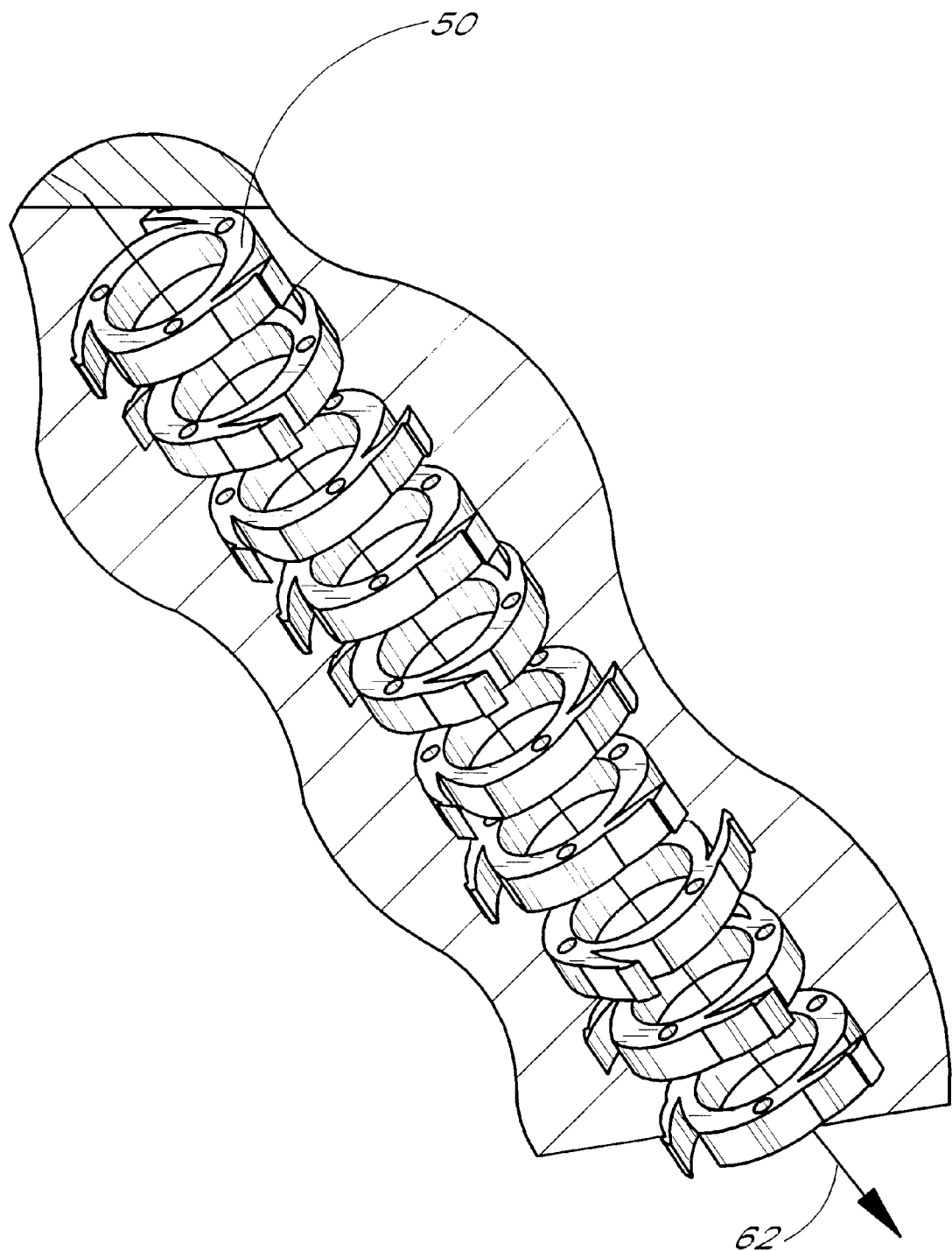
Figure 22:
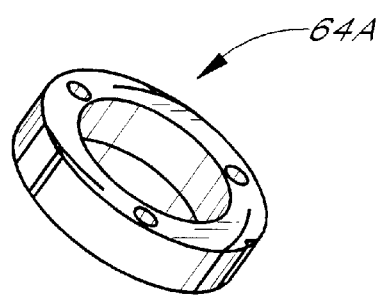
FIG. 22 is a perspective view of a ring of a bulkhead stent in a loaded configuration
Figure 23:
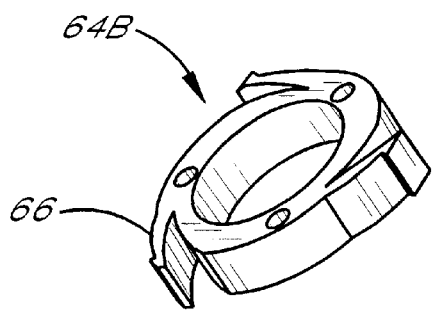
FIG. 23 is a perspective view of a ring of a bulkhead stent in an inserted configuration.

Turning now to FIGS. 14–26, there is illustrated in greater detail one preferred method and apparatus for providing a bulkhead stent 50, as shown in FIG. 12, into the myocardium MYO. As shown in FIG. 14, a stent delivery catheter 60 is advanced over a puncture wire 62 and into the wall of the myocardium MYO as described above. The stent delivery catheter 60 follows the path created by the puncture wire 62 used to form the passage between the coronary artery CA and the left ventricle LV. FIG. 15 illustrates a bulkhead stent 50 still located in position inside the stent delivery catheter 60 with the catheter 60 in position in the heart wall MYO. FIGS. 16–19 show one embodiment for deploying the bulkhead stent 50 into the myocardium MYO. As the delivery catheter 60 is retracted proximally from the myocardium MYO, the rings comprising the bulkhead stent 50 are deployed into the myocardium MYO. FIGS. 20 and 21 are enlarged views of FIGS. 18 and 19, showing the rings of the bulkhead stent 50 positioned within the myocardium MYO to form the passageway therethrough.

Figure 24:
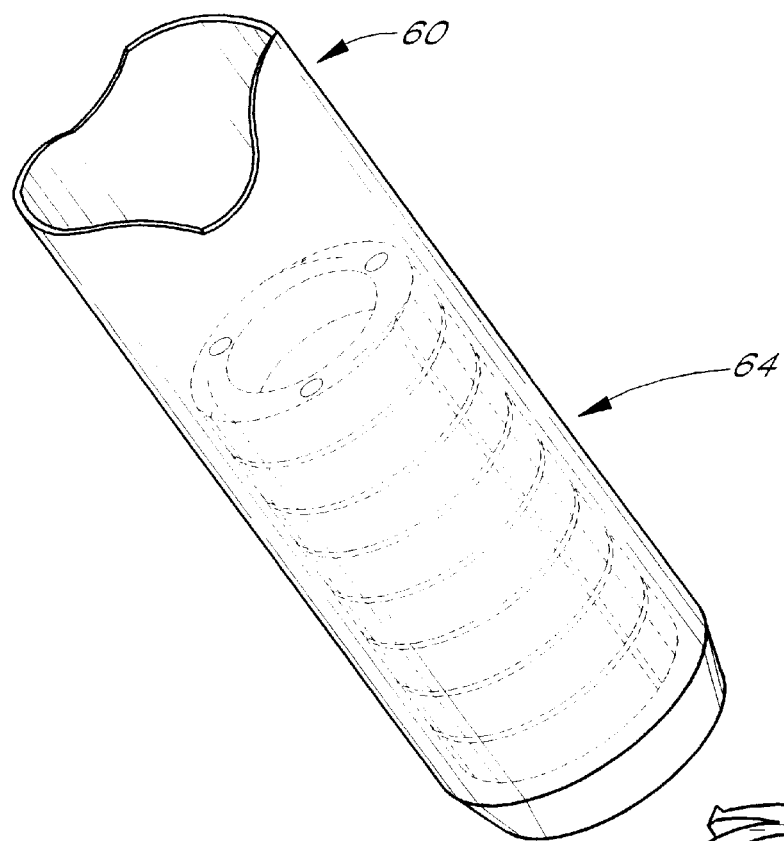
FIG. 24 is a perspective view of a bulkhead stent within a delivery catheter, showing the rings of the bulkhead stent being inserted.
Figure 25:
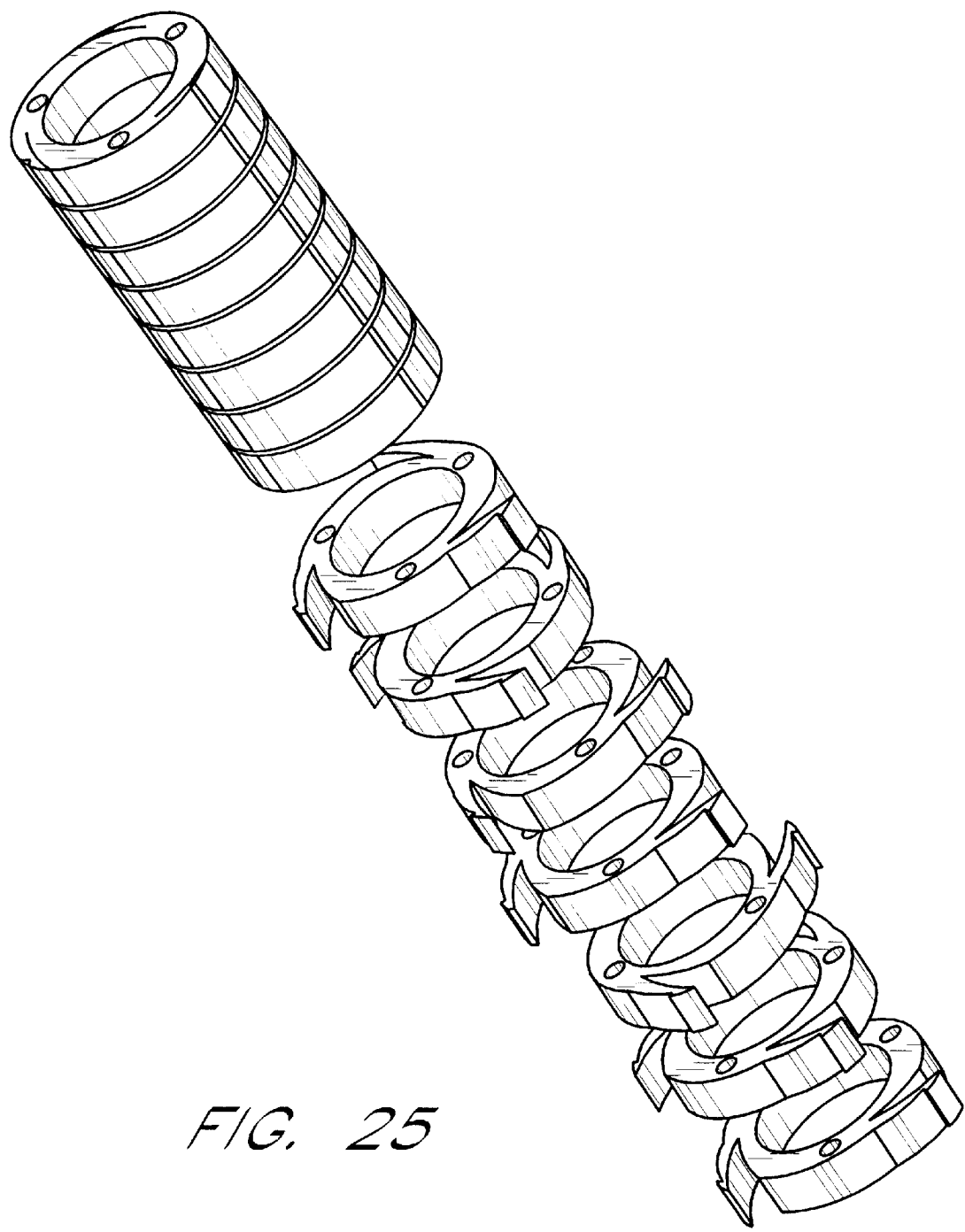
FIG. 25 is a perspective view of a bulkhead stent, with the rings of the stent in loaded and inserted configurations.

FIGS. 22-25 illustrate more particularly the structure and deployment of the rings comprising the bulkhead stent 50. As shown in FIG. 24, the bulkhead stent comprises a plurality of rings 64 that are initially loaded into the delivery catheter 60. While inside the lumen of the catheter 60, each ring 64 has a loaded configuration 64A, shown in FIGS. 22 and 25. After ejectment from the catheter 60, the ring 64 assumes an inserted configuration 64B, shown in FIGS. 23 and 25. Preferably, the inserted configuration of ring 64B includes a plurality of flanges 66 around the circumference of each ring 64, thereby providing a securement mechanism to anchor each ring 64 to the myocardium MYO. Each ring 64 transforms from its loaded configuration 64A to its inserted configuration 64B by virtue of being released from the catheter 60. Specifically, the catheter 60 acts as a restraint on each ring 64 to keep it in its loaded configuration 64A. Then, once the ring 64 is released from the catheter 60, the flanges 66 provided along the circumference of each ring 64 are allowed to extend outward to provide the securement mechanism.

Figure 26:
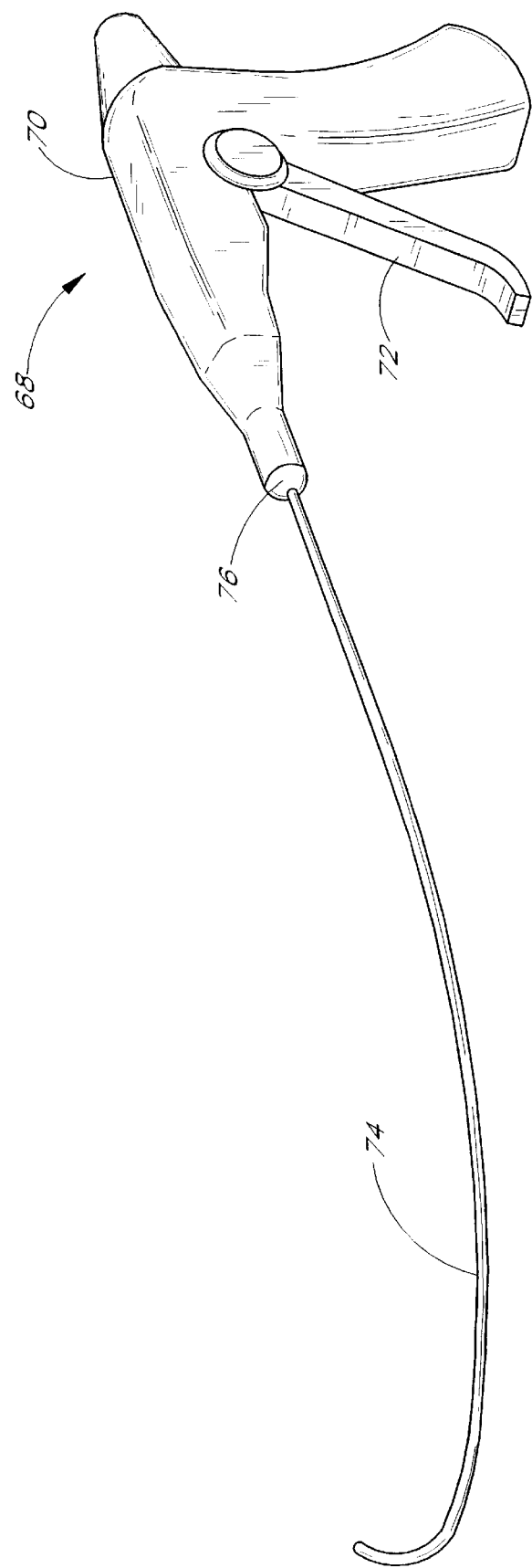
FIG. 26 is a perspective view of an inserter device used to insert a bulkhead stent.
Figure 27A:
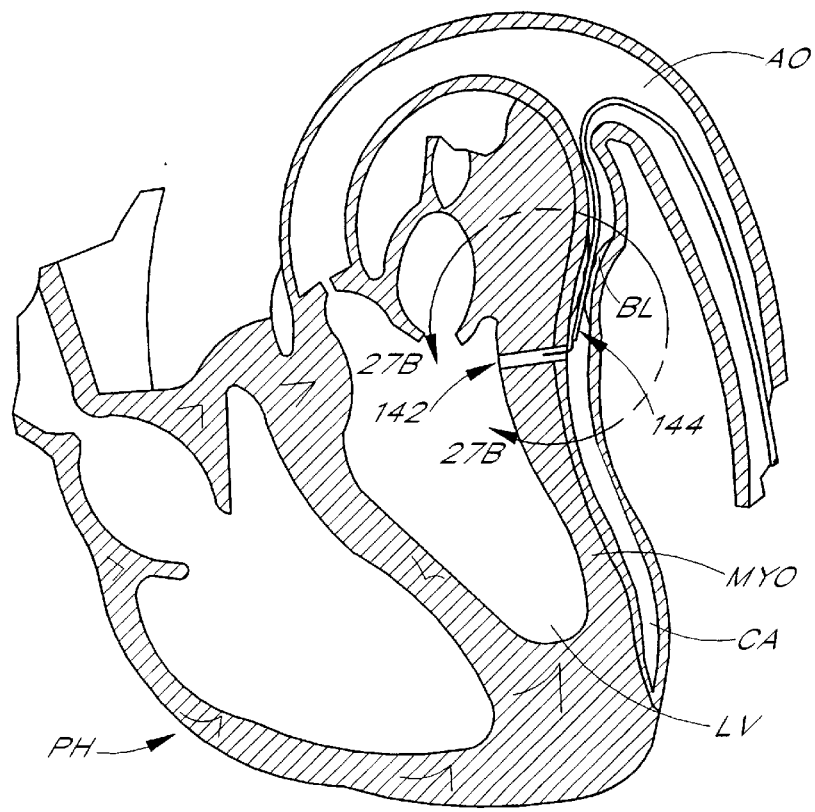
FIG. 27A is a schematic, cross-sectional view of the human heart, showing a catheter used to form a channel through the myocardium and into the left ventricle inserted into the coronary artery.
Figure 27B:
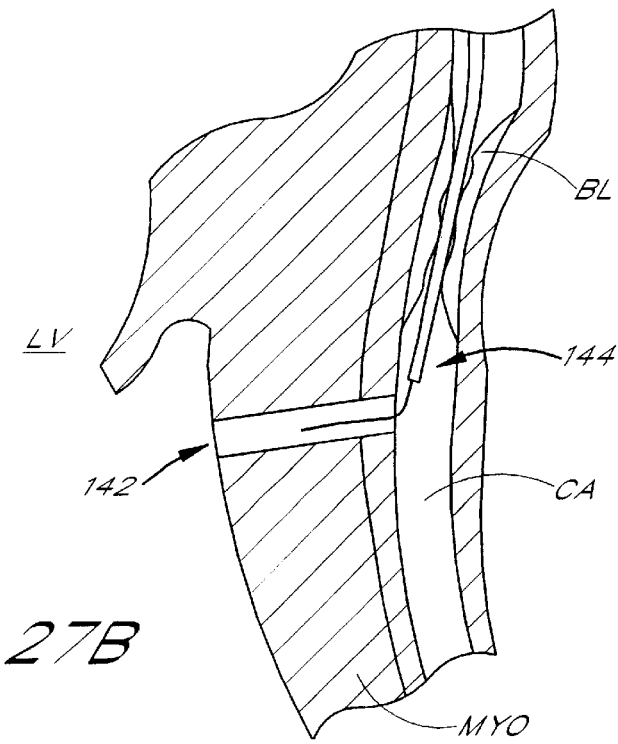
FIG. 27B is an enlarged view of the distal end of the catheter and the channel through the myocardium in FIG. 27A.

FIG. 26 illustrates an inserter device or handle 68 that may be used in deploying the bulkhead stent 50 into the myocardium. The inserter handle 68 preferably comprises a gun 70 with a trigger 72, and a wire 74 extending from a nozzle 76. The rings 64 (not shown) of the bulkhead stent 50 are preferably loaded onto the wire 74, and may be deployed into the myocardium preferably one at a time by pressing the trigger 72.

Figure 28:
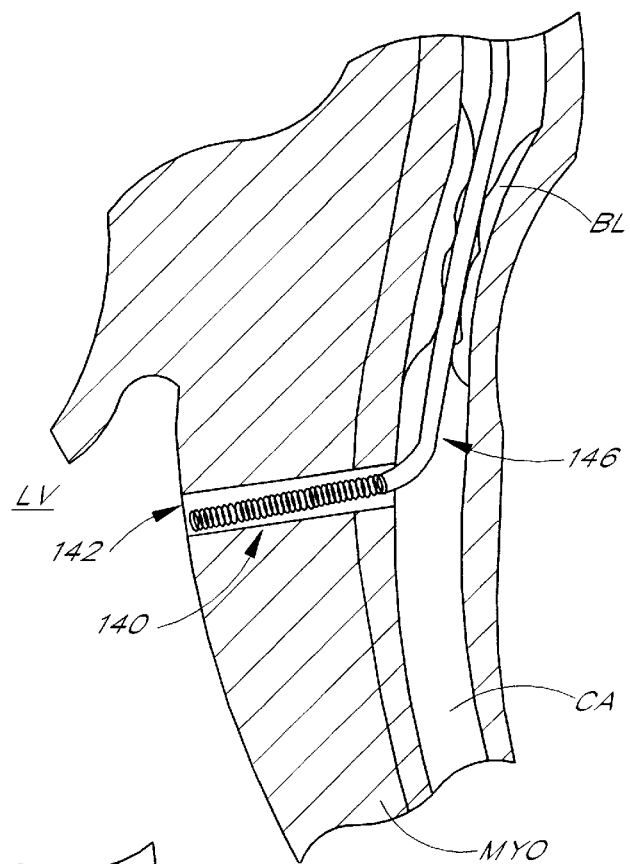
FIG. 28 is a schematic, cross-sectional view of a stent delivery catheter positioned inside the channel formed in the myocardium.
Figure 29:
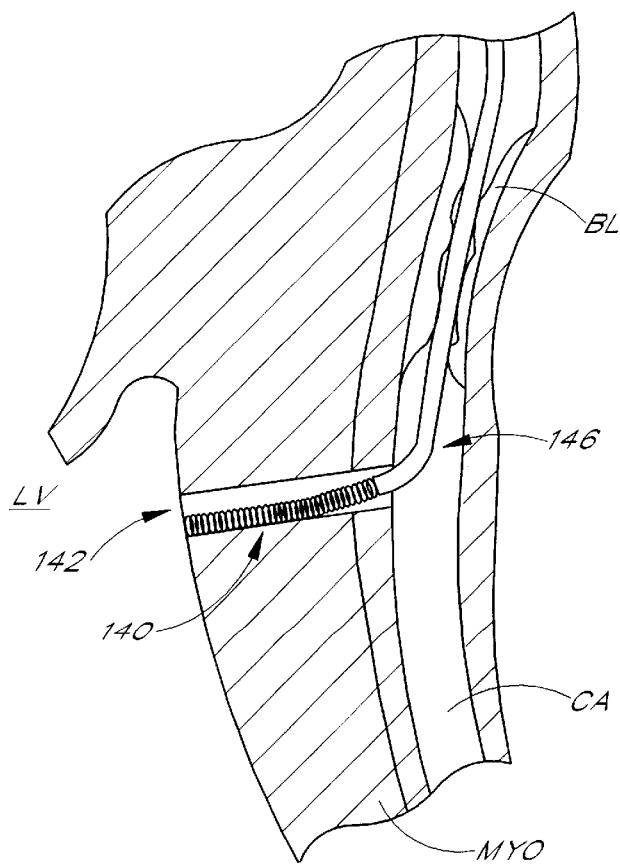
FIG. 29 is a schematic, partial cross-sectional view of a self-expanding spring stent being positioned in the channel formed in the myocardium.
Figure 30:
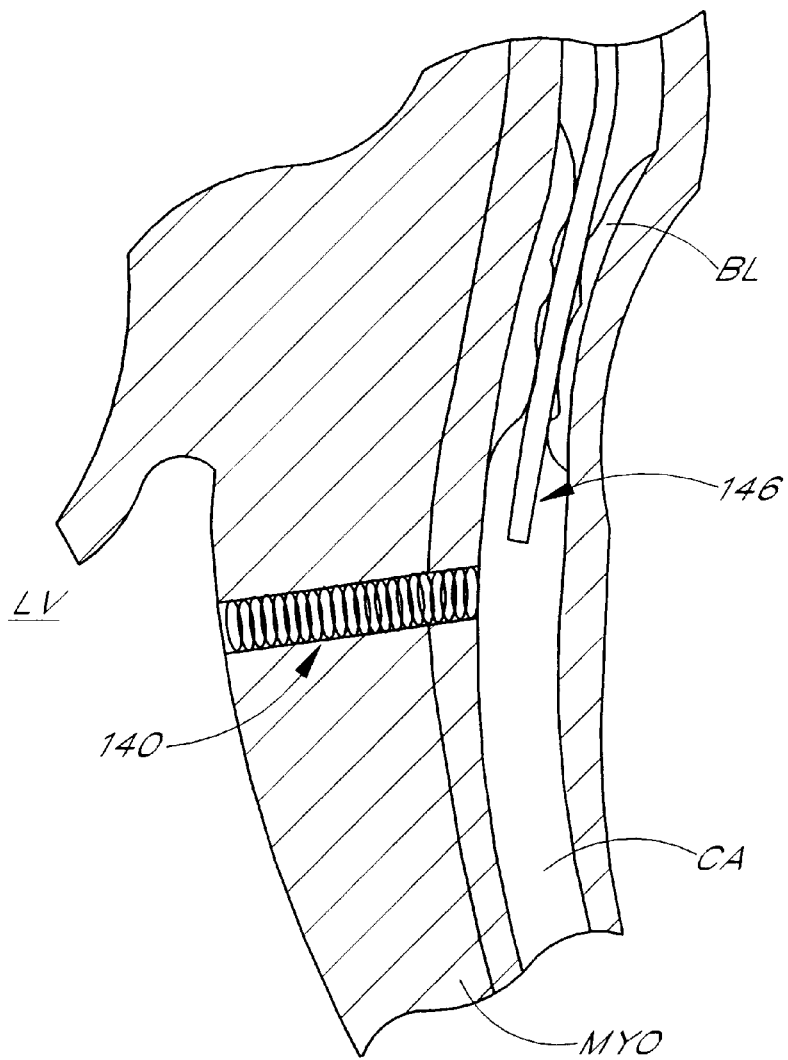
FIG. 30 is a schematic, partial cross-sectional view of the self-expanding stent deployed within the myocardium.

FIGS. 27–30 illustrate another embodiment of the present invention. Here, a self-expanding spring or screw stent 140 is delivered into the myocardium MYO. As illustrated in FIG. 27A, a channel 142 through the wall of the myocardium MYO is first created, as described above, using a device 144 delivered through the aorta AO and coronary artery CA. The channel 142 travels from the coronary artery CA through the myocardium MYO and into the left ventricle LV as shown in FIG. 27B. The distal end of the stent delivery catheter 146 bearing the stent 140 is then positioned within the channel 142, as shown in FIG. 28. Preferably, the position of the distal end of the delivery catheter 146 is checked radiographically, to ensure proper positioning. Next, as illustrated in FIG. 29, the self-expanding spring stent 140 is delivered into the channel 142 wall of the myocardium MYO. The stent 140 is cut such that it does not extend past the myocardium MYO and into either the left ventricle LV or the coronary artery CA. Again, the proper positioning and length of the stent 140 is preferably checked radiographically and any necessary adjustments made before the delivery catheter 146 is removed, as shown in FIG. 30.

Figure 31:
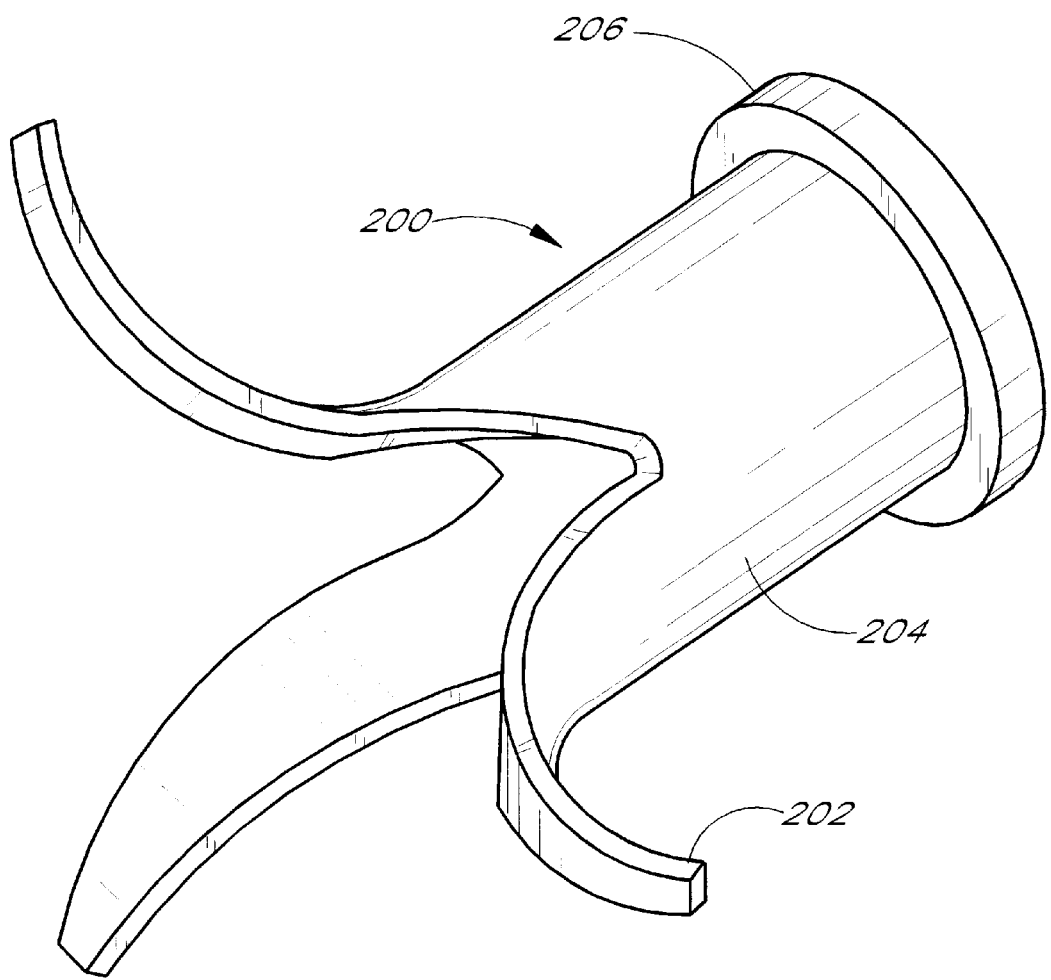
FIG. 31 is a perspective view of another embodiment of a stent having retention members which maintain the position of the stent.

FIG. 31 illustrates another embodiment of the stent 200 having retention members 202. The hollow stent body 204 is held in place in the heart wall by one or more retention members 202 which are deployed after the stent 200 is properly positioned, as described above. FIG. 31 shows the retention members 202 in their deployed position. A flange 206 acts to seal the opening in the coronary artery, while the retention members 202 reside in the myocardium, helping to anchor the stent 200 in place.

It should be appreciated that the stents described above, and particularly the bulkhead stent, are useful in other applications in addition to stenting the myocardium. For example, these stents may also serve as other types of coronary stents, arterial or venous stents, as well as billiary and esophageal stents.

The present vascular shunt provides significant improvements in the present treatment of blockages in the coronary artery. Although the invention has been described in its preferred embodiments in connection with the particular figures, it is not intended that this description should be limited in any way.

What is claimed is:

1. A bypass conduit for use in a wall of a heart, comprising:

a hollow conduit having an interior and an exterior and adapted to be positioned in the heart wall between the coronary artery and a chamber in the heart, wherein the conduit has an attachment mechanism on at least one end adapted to anchor the conduit in place.

2. The device of claim 1, wherein the conduit is self-expandable.

3. The device of claim 1, wherein the conduit is expanded using an inflatable balloon.

4. The device of claim 1, wherein the chamber is the left ventricle.

5. The device of claim 1, wherein the attachment mechanism is selected from the group consisting of hooks, barbs, flanges, collars, suture holes, and expandable legs.

6. A bypass conduit for use in a wall of a heart, comprising:

a hollow conduit having a plurality of circular rings, an interior, and an exterior and adapted to be positioned in the heart wall between the coronary artery and a chamber in the heart, wherein the conduit has an attachment mechanism on at least one end adapted to anchor the conduit in place.

7. The device of claim 6, wherein the rings are reversibly connected to one another.

8. The device of claim 1, wherein the conduit is biodegradable.

9. The device of claim 1, wherein the conduit is bioabsorbable.

10. The device of claim 9, wherein the conduit is used to deliver pharmaceutical compounds directly into the heart wall.

11. The device of claim 1, wherein the attachment mechanism is adapted to anchor the conduit in the heart wall.

12. The device of claim 1, wherein the attachment mechanism is adapted to anchor the conduit in the coronary artery.

* * * * *

Disclaimer

6,290,728 — David Y. Phelps; Greg R. Furnish, both of Louisville; Todd A. Hall, Goshen; Mark Griffin, Louisville, all of KY; Scott J. Wolf, Minneapolis, MN; Peter J. Wilk, New York, NY; Jay Schmelter, Plymouth, MN; Simon Furnish, Louisville, KY. DESIGNS FOR LEFT VENTRICULAR CONDUIT. Patent dated Sep. 18, 2001. Disclaimer filed July 20, 2004, by the assignee, Percardia, Inc.

Hereby enters this disclaimer to claims 1, 3, 4, 5, 6, 11, and 12 of said patent.

*(Official Gazette May 24, 2005)*